(12) United States Patent
Fuji et al.

(10) Patent No.: US 10,481,027 B2
(45) Date of Patent: Nov. 19, 2019

(54) SENSOR, ELECTRONIC DEVICE, MICROPHONE, BLOOD PRESSURE SENSOR, AND TOUCH PANEL

(71) Applicant: Kabushiki Kaisha Toshiba, Tokyo (JP)

(72) Inventors: Yoshihiko Fuji, Kanagawa (JP); Michiko Hara, Kanagawa (JP); Kei Masunishi, Kanagawa (JP); Yoshihiro Higashi, Ishikawa (JP); Shiori Kaji, Kanagawa (JP); Akiko Yuzawa, Kanagawa (JP); Akio Hori, Kanagawa (JP); Tomohiko Nagata, Kanagawa (JP); Kazuaki Okamoto, Kanagawa (JP); Kenji Otsu, Kanagawa (JP); Shotaro Baba, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 16/145,763

(22) Filed: Sep. 28, 2018

(65) Prior Publication Data

US 2019/0041285 A1    Feb. 7, 2019

Related U.S. Application Data

(62) Division of application No. 15/248,412, filed on Aug. 26, 2016, now Pat. No. 10,145,751.

(30) Foreign Application Priority Data

Sep. 4, 2015    (JP) .................................. 2015-174549

(51) Int. Cl.
*A61B 5/021* (2006.01)
*G01L 9/00* (2006.01)
(Continued)

(52) U.S. Cl.
CPC ............ *G01L 9/0091* (2013.01); *A61B 5/021* (2013.01); *A61B 5/6898* (2013.01); *H04R 1/46* (2013.01)

(58) Field of Classification Search
CPC ......... A61B 5/021; A61B 5/6898; G01L 9/00; G01L 9/0091; G01L 9/16; H04R 1/46; H04R 21/02
See application file for complete search history.

(56) References Cited

U.S. PATENT DOCUMENTS 5,024,100 A * 6/1991 Weinstein ............... G01L 19/02
                                                              73/724
6,640,643 B2   11/2003 Ishio et al.
(Continued)

FOREIGN PATENT DOCUMENTS

JP    2002-148132 A    5/2002
JP    2003-28740 A     1/2003
(Continued)

OTHER PUBLICATIONS

Meyners et al., "Pressure Sensor Based on Magnetic Tunnel Junctions", Journal of Applied Physics, vol. 105, No. 7, pp. C914-1 to C914-3, (2000).
(Continued)

*Primary Examiner* — Nguyen Q. Ha
(74) *Attorney, Agent, or Firm* — Finnegan, Henderson, Farabow, Garrett & Dunner, L.L.P.

(57) ABSTRACT

According to one embodiment, a sensor includes a deformable film portion, a first sensing element and a second sensing element. The first sensing element is fixed to the film portion, and includes a first magnetic layer of a first material, a first opposing magnetic layer, and a first intermediate layer. The first intermediate layer is provided between the first magnetic layer and the first opposing magnetic layer. The second sensing element is fixed to the film portion, and (Continued)

includes a second magnetic layer of a second material, a second opposing magnetic layer, and a second intermediate layer. The second material is different from the first material. The second intermediate layer is provided between the second magnetic layer and the second opposing magnetic layer.

20 Claims, 10 Drawing Sheets

(51) Int. Cl.
  *G01L 9/16* (2006.01)
  *H04R 21/02* (2006.01)
  *H04R 1/46* (2006.01)
  *A61B 5/00* (2006.01)

(56) References Cited

U.S. PATENT DOCUMENTS

| | | |
|---|---|---|
| 2003/0015040 A1 | 1/2003 | Ishio et al. |
| 2007/0186666 A1 | 8/2007 | Ruehrig |
| 2011/0295128 A1 | 12/2011 | Yuasa |
| 2012/0079887 A1 | 4/2012 | Giddings |
| 2013/0255393 A1 | 10/2013 | Fukuzawa et al. |
| 2015/0047437 A1 | 2/2015 | Fukuzawa et al. |
| 2015/0082900 A1* | 3/2015 | Fuji .................. G01L 9/007 73/779 |
| 2015/0082918 A1 | 3/2015 | Fuji et al. |
| 2015/0088008 A1* | 3/2015 | Fuji .................... G01L 9/16 600/485 |
| 2015/0271586 A1 | 9/2015 | Fukuzawa et al. |
| 2015/0338293 A1* | 11/2015 | Masunishi ............ G01L 1/22 73/649 |
| 2016/0003697 A1* | 1/2016 | Okamoto ........... G01L 9/0041 73/862.632 |
| 2016/0009545 A1* | 1/2016 | Fuji ................. G01L 9/0042 257/419 |

FOREIGN PATENT DOCUMENTS

| | | |
|---|---|---|
| JP | 2013-205403 A | 10/2013 |
| JP | 2015-61056 A | 3/2015 |
| JP | 2015-184067 A | 10/2015 |

OTHER PUBLICATIONS

Löhndorf et al., "Highly Sensitive Strain Sensors Based on Magnetic Tunneling Junctions", Applied Physics Letters, vol. 81, No. 2, pp. 313-315, (2002).

* cited by examiner

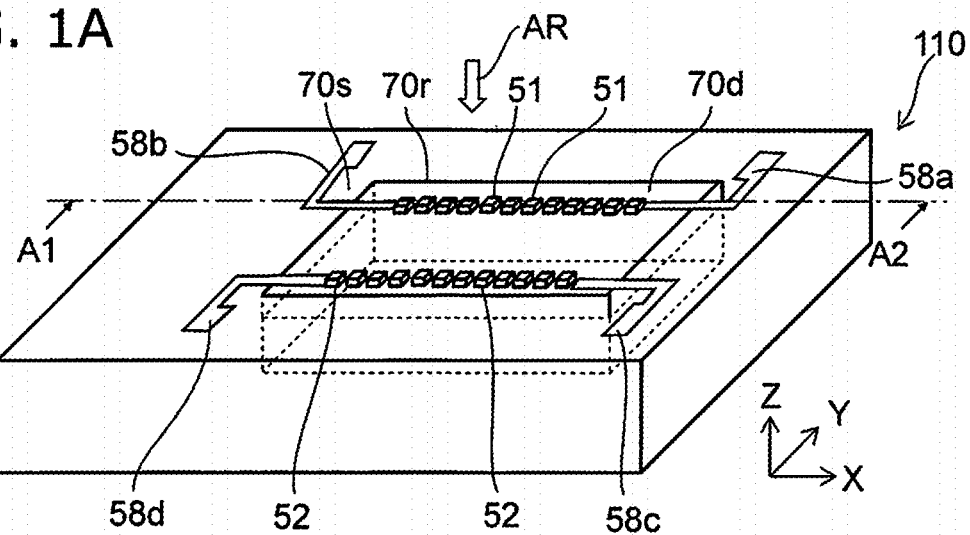
FIG. 1A
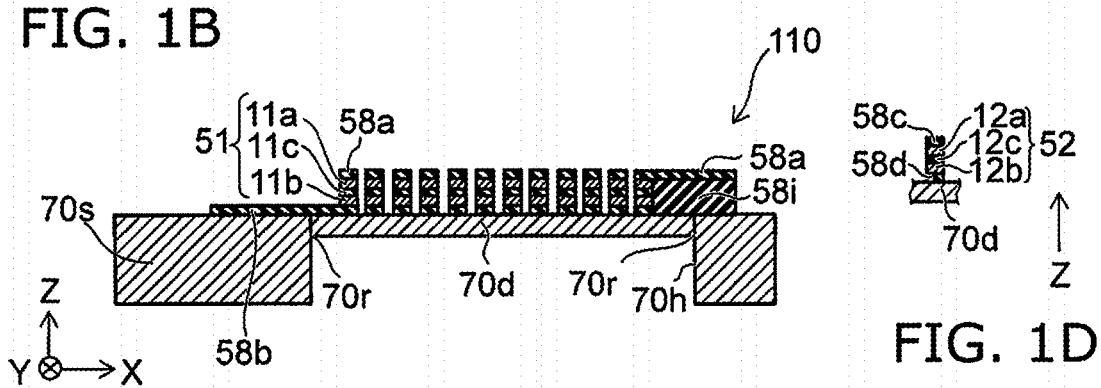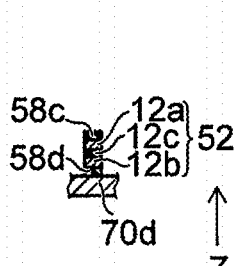
FIG. 1B
FIG. 1D
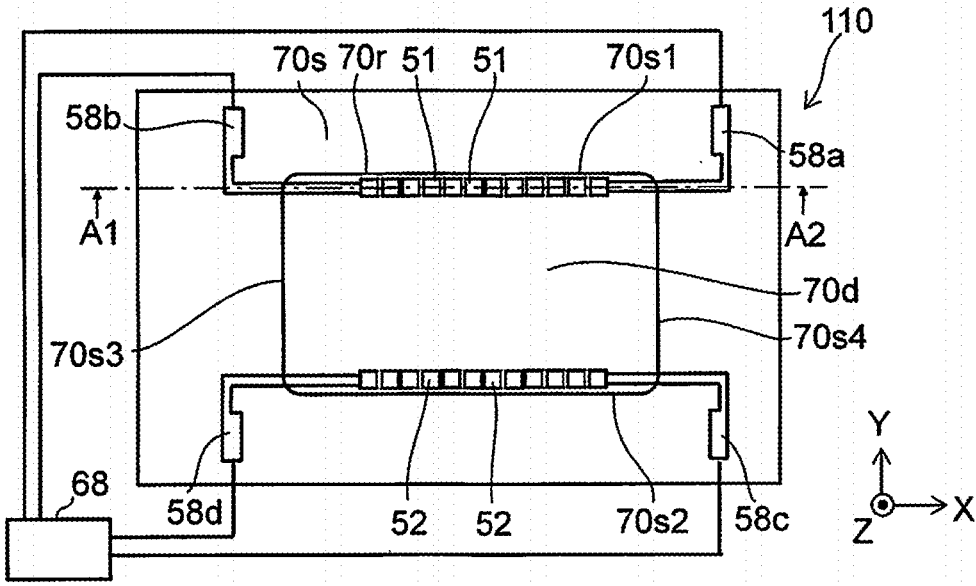
FIG. 1C

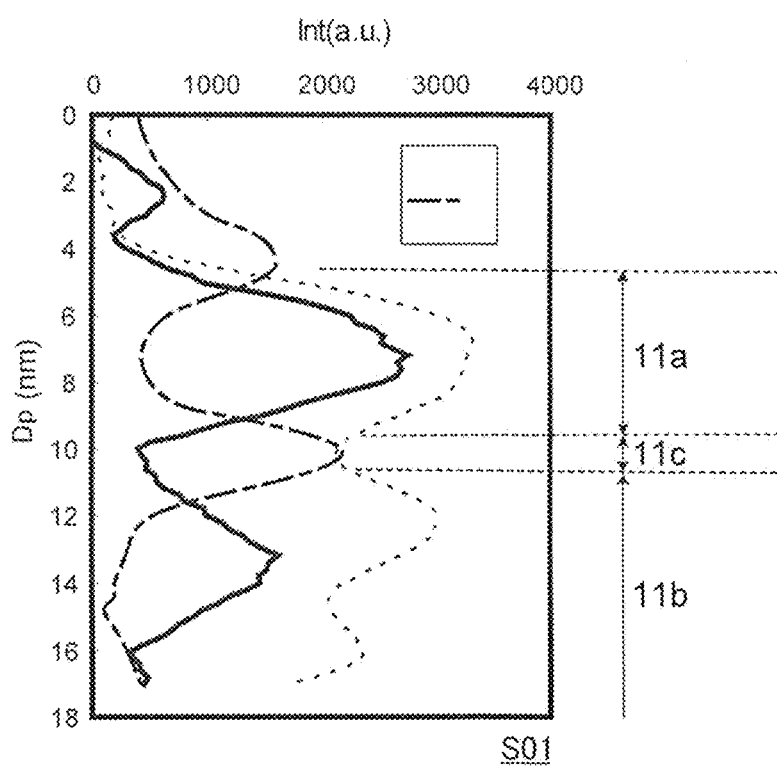 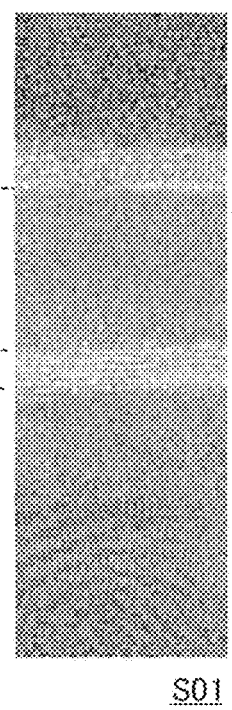
FIG. 2A  FIG. 2B
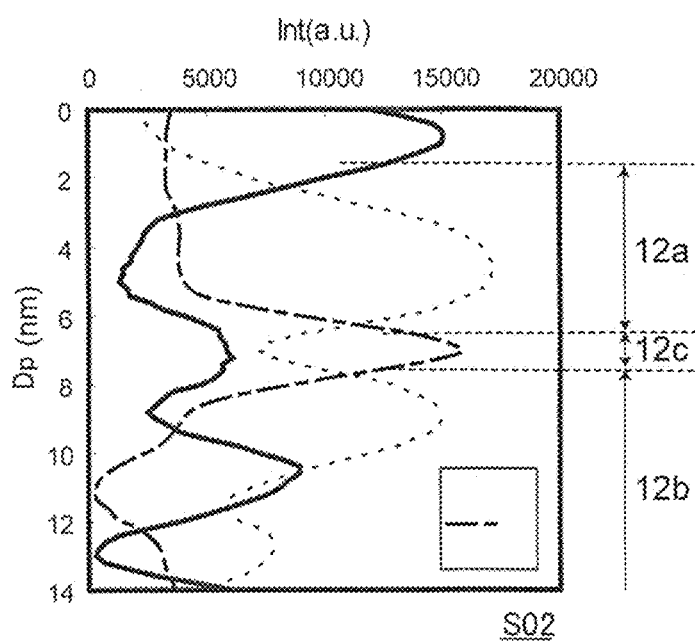 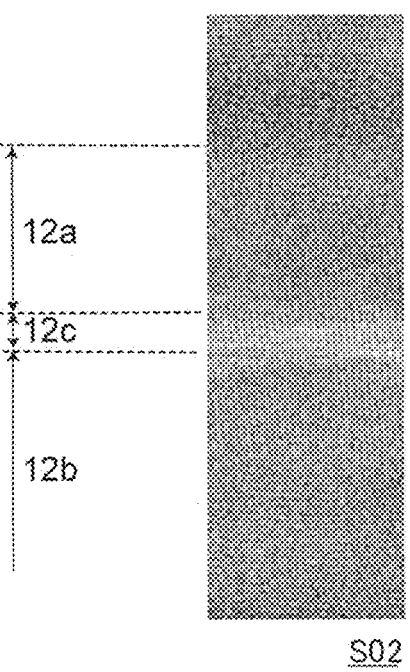
FIG. 2C  FIG. 2D

FIG. 5
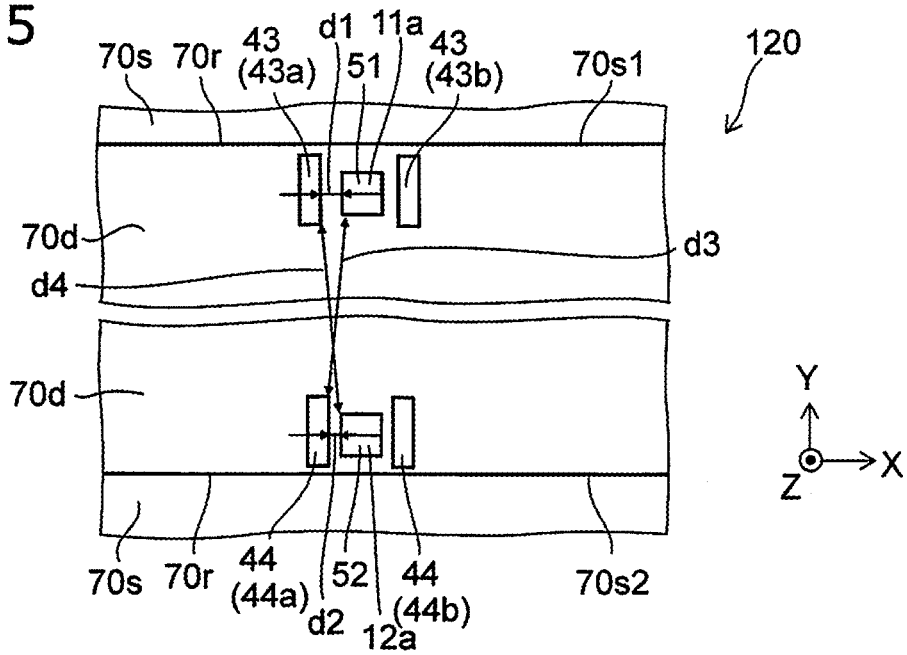
FIG. 6A
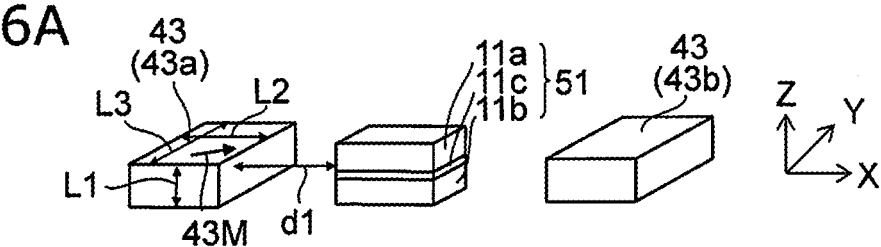
FIG. 6B
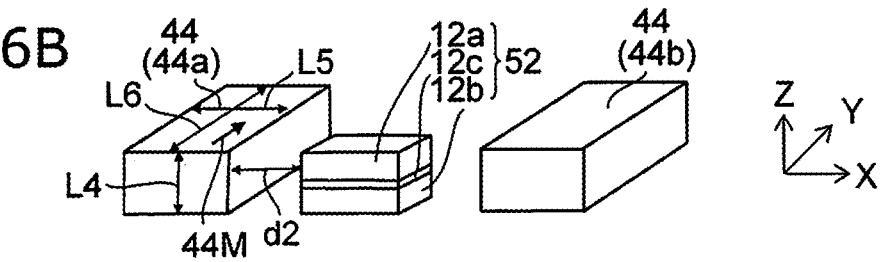
FIG. 6C
FIG. 6D
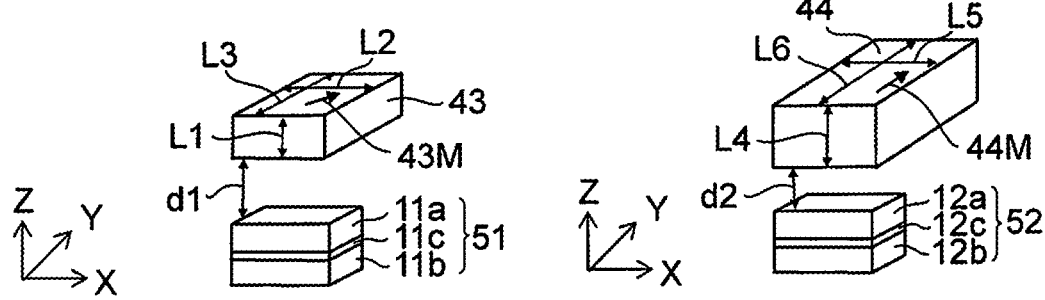

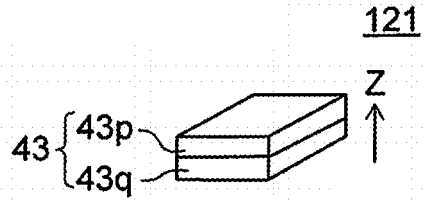
FIG. 7A
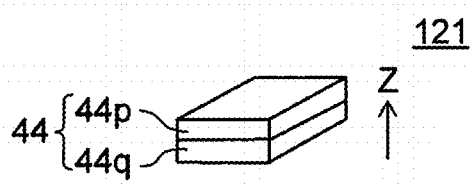
FIG. 7B
FIG. 8
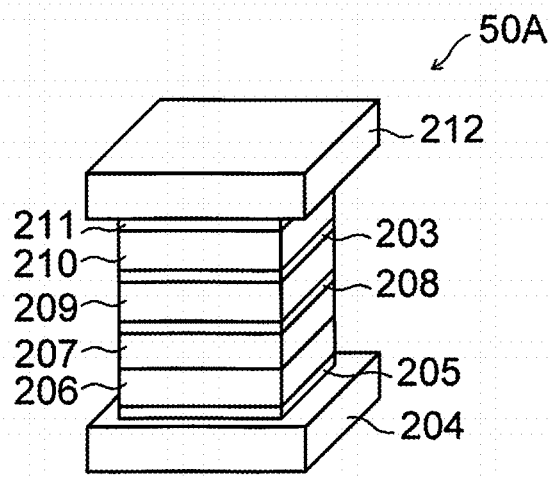
FIG. 9
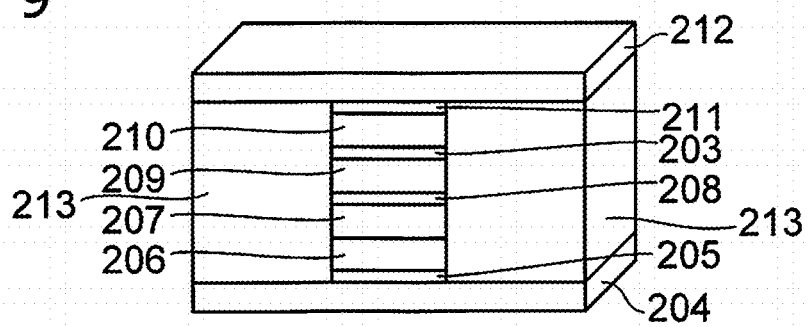
FIG. 10
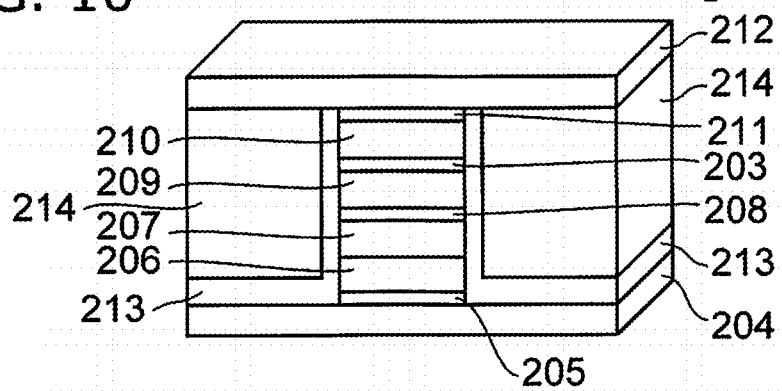

FIG. 15
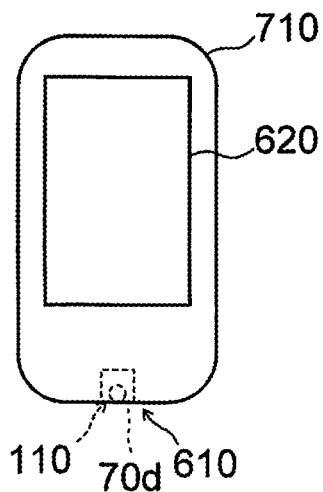
FIG. 16
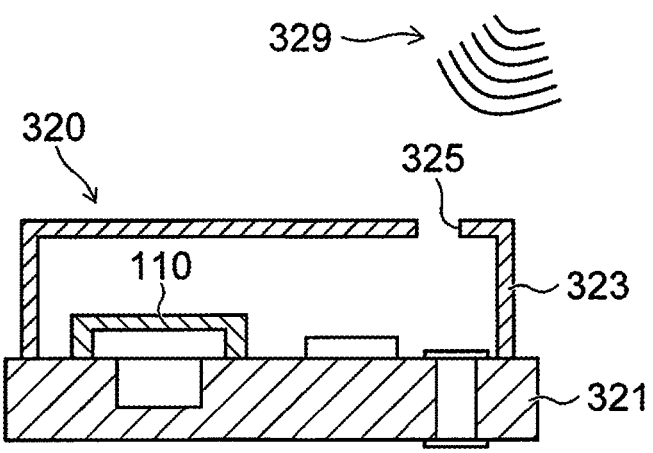
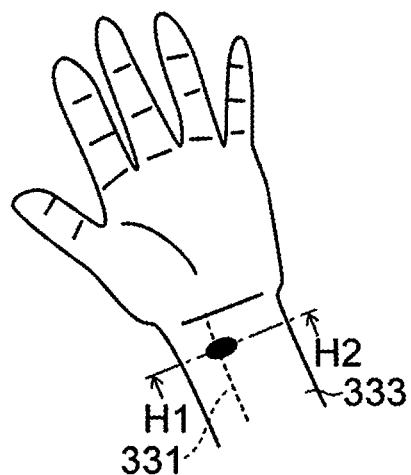
FIG. 17A
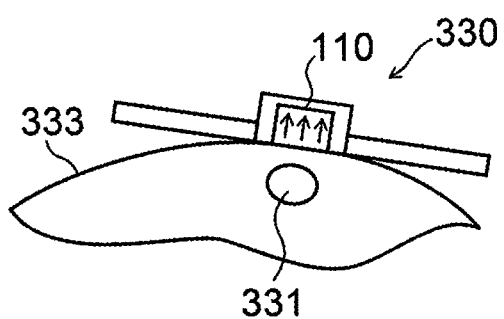
FIG. 17B

SENSOR, ELECTRONIC DEVICE, MICROPHONE, BLOOD PRESSURE SENSOR, AND TOUCH PANEL

CROSS-REFERENCE TO RELATED APPLICATIONS

This application is a division of U.S. application Ser. No. 15/248,412, filed Aug. 26, 2016, which is based upon and claims the benefit of priority from Japanese Patent Application No. 2015-174549, filed on Sep. 4, 2015; the entire contents of which are incorporated herein by reference.

FIELD

Embodiments described herein relate generally to a sensor, an electronic device, a microphone, a blood pressure sensor, and a touch panel.

BACKGROUND

A sensor that uses a magnetic layer has been proposed. For example, the sensor is applied to a microphone, a blood pressure sensor, a touch panel, etc. It is desirable for the pressure sensor to have a wide dynamic range.

BRIEF DESCRIPTION OF THE DRAWINGS

FIG. 1A to FIG. 1D are schematic views illustrating a pressure sensor according to a first embodiment;

FIG. 2A to FIG. 2D are schematic views illustrating the pressure sensor according to the first embodiment;

FIG. 5 is a schematic plan view illustrating a pressure sensor according to a second embodiment;

FIG. 6A to FIG. 6D are schematic perspective views illustrating the pressure sensor according to the second embodiment;

FIG. 7A and FIG. 7B are schematic perspective views illustrating portions of another pressure sensor according to the second embodiment;

FIG. 8 is a schematic perspective view illustrating a portion of the pressure sensor according to the embodiment;

FIG. 9 is a schematic perspective view illustrating a portion of another pressure sensor according to the embodiment;

FIG. 10 is a schematic perspective view illustrating a portion of another pressure sensor according to the embodiment;

FIG. 15 is a schematic view illustrating a microphone according to a third embodiment;

FIG. 16 is a schematic cross-sectional view illustrating another microphone according to the third embodiment;

FIG. 17A and FIG. 17B are schematic views illustrating a blood pressure sensor according to a fourth embodiment;

DETAILED DESCRIPTION

Figure 3A:
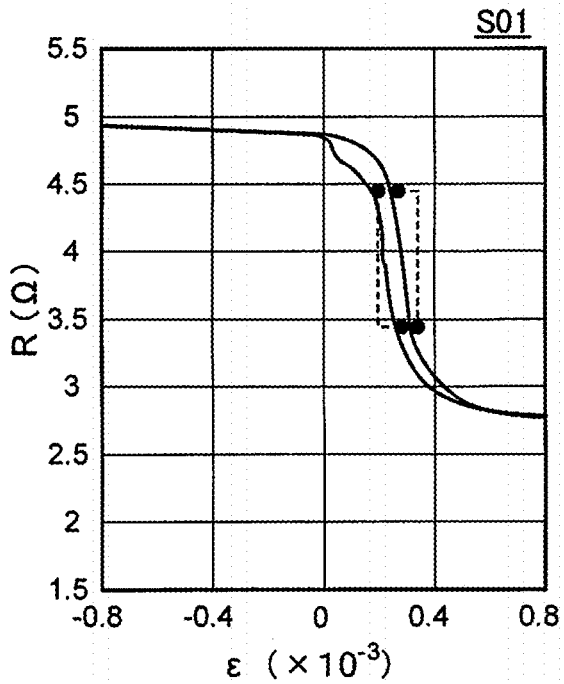
FIG. 3A and FIG. 3B are schematic views illustrating the pressure sensor according to the first embodiment.

According to one embodiment, a sensor includes a deformable film portion, a first sensing element and a second sensing element. The first sensing element is fixed to the film portion, and includes a first magnetic layer of a first material, a first opposing magnetic layer, and a first intermediate layer. The first intermediate layer is provided between the first magnetic layer and the first opposing magnetic layer. The second sensing element is fixed to the film portion, and includes a second magnetic layer of a second material, a second opposing magnetic layer, and a second intermediate layer. The second material is different from the first material. The second intermediate layer is provided between the second magnetic layer and the second opposing magnetic layer.

According to one embodiment, a sensor includes a film portion, a first sensing element, a second sensing element, a third magnetic layer, and a fourth magnetic layer. The film portion is deformable. The first sensing element is fixed to the film portion. The first sensing element includes a first magnetic layer, a first opposing magnetic layer, and a first intermediate layer. The first intermediate layer is provided between the first magnetic layer and the first opposing magnetic layer. The second sensing element is fixed to the film portion. The second sensing element includes a second magnetic layer, a second opposing magnetic layer, and a second intermediate layer. The second intermediate layer is provided between the second magnetic layer and the second opposing magnetic layer. The third magnetic layer has a first length along a first direction, the first direction being from the film portion toward the first sensing element, a second length along a second direction perpendicular to the first direction, a third length along a third direction perpendicular to the first direction and perpendicular to the second direction, a first composition, and a third magnetization direction. The fourth magnetic layer has at least one of a fourth length along the first direction, the fourth length being different from the first length, a fifth length along the second direction, the fifth length being different from the second length, a sixth length along the third direction, the sixth length being different from the third length, a second composition different from the first composition, or a fourth magnetization direction different from the third magnetization direction.

According to one embodiment, a sensor, includes c a film portion, a first sensing element, a second sensing element, a third magnetic layer, and a fourth magnetic layer. The film portion is deformable. The first sensing element is fixed to the film portion. The first sensing element includes a first magnetic layer, a first opposing magnetic layer, and a first intermediate layer. The first intermediate layer is provided between the first magnetic layer and the first opposing magnetic layer. The second sensing element is fixed to the film portion. The second sensing element includes a second magnetic layer, a second opposing magnetic layer, and a second intermediate layer. The second intermediate layer is provided between the second magnetic layer and the second opposing magnetic layer. The third magnetic layer includes at least one selected from the group consisting of a first alloy, a second alloy, a third alloy, and a fourth alloy, the first alloy including Co and Pt, the second alloy including Fe and Pt, the third alloy including Co and Pd, the fourth alloy including Fe and Pd. The fourth magnetic layer includes at least one selected from the group consisting of a sixth alloy, a seventh alloy, an eighth alloy, and a ninth alloy, the sixth alloy including Co and Pt, the seventh alloy including Fe and Pt, the eighth alloy including Co and Pd, the ninth alloy including Fe and Pd. The third magnetic layer has a first distance between the first magnetic layer and the third magnetic layer. The fourth magnetic layer has a second distance between the second magnetic layer and the fourth magnetic layer. The second distance is different from the first distance. The first distance is shorter than a distance between the first magnetic layer and the fourth magnetic layer. The second distance is shorter than a distance between the second magnetic layer and the third magnetic layer.

According to one embodiment, a sensor, includes c a film portion, a first sensing element, a second sensing element, a third magnetic layer, and a fourth magnetic layer. The film portion is deformable. The first sensing element is fixed to the film portion. The first sensing element includes a first magnetic layer, a first opposing magnetic layer, and a first intermediate layer. The first intermediate layer is provided between the first magnetic layer and the first opposing magnetic layer. The second sensing element is fixed to the film portion. The second sensing element includes a second magnetic layer, a second opposing magnetic layer, and a second intermediate layer. The second intermediate layer is provided between the second magnetic layer and the second opposing magnetic layer. The third magnetic layer includes a first film and a second film. The first film includes at least one of Fe, Co, or Ni, and the second film including at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O. The fourth magnetic layer includes a third film and a fourth film. The third film includes at least one of Fe, Co, or Ni. The fourth film includes at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O. The third magnetic layer has a first distance between the first magnetic layer and the third magnetic layer. The fourth magnetic layer has a second distance between the second magnetic layer and the fourth magnetic layer, the second distance being different from the first distance. The first distance is shorter than a distance between the first magnetic layer and the fourth magnetic layer. The second distance is shorter than a distance between the second magnetic layer and the third magnetic layer.

According to one embodiment, a sensor includes a film portion, a first sensing element, a second sensing element, and a processor. The film portion is deformable. The first sensing element is fixed to the film portion. The first sensing element includes a first magnetic layer, a first opposing magnetic layer, and a first intermediate layer. The first intermediate layer is provided between the first magnetic layer and the first opposing magnetic layer. The second sensing element is fixed to the film portion. The second sensing element includes a second magnetic layer, a second opposing magnetic layer, and a second intermediate layer. The second intermediate layer is provided between the second magnetic layer and the second opposing magnetic layer. The processor is connected to the first sensing element and the second sensing element. The processor implements a first operation and a second operation. The first operation outputs a first output signal corresponding to a first signal obtained from the first sensing element. The second operation outputs a second output signal corresponding to a second signal obtained from the second sensing element.

Various embodiments will be described hereinafter with reference to the accompanying drawings.

The drawings are schematic and conceptual; and the relationships between the thickness and width of portions, the proportions of sizes among portions, etc., are not necessarily the same as the actual values thereof. Further, the dimensions and proportions may be illustrated differently among drawings, even for identical portions.

In the present specification and drawings, the same elements as those described previously with reference to earlier figures are labeled with like reference numerals, and the detailed description thereof is omitted as appropriate.

First Embodiment

FIG. 1A to FIG. 1D are schematic views illustrating a pressure sensor according to a first embodiment.

FIG. 1A is a perspective view. FIG. 1B is a line A1-A2 cross-sectional view of FIG. 1A. FIG. 1C is a plan view as viewed along arrow AR of FIG. 1A. FIG. 1D is a cross-sectional view illustrating a portion of the pressure sensor.

As shown in FIG. 1A, the pressure sensor 110 (sensor) according to the embodiment includes a film portion 70d, a first sensing element 51, and a second sensing element 52.

The film portion 70d is deformable. The first sensing element 51 is fixed to the film portion 70d. The second sensing element 52 is fixed to the film portion 70d. In the example, the first sensing element 51 is fixed to a first position (a first region) of the film portion 70d. The second sensing element 52 is fixed to a second position (a second region) of the film portion 70d.

The first sensing element 51 is provided on a portion of the film portion 70d. The second sensing element 52 is provided on another portion of the film portion 70d.

A direction from the film portion 70d toward the first sensing element 51 is taken as a Z-axis direction. One direction perpendicular to the Z-axis direction is taken as an X-axis direction. A direction perpendicular to the Z-axis direction and the X-axis direction is taken as a Y-axis direction.

In the example, multiple first sensing elements 51 and multiple second sensing elements 52 are provided. In the example, the multiple first sensing elements 51 are arranged along the X-axis direction. In the example, the multiple second sensing elements 52 are arranged along the X-axis direction. For example, the second sensing element 52 is arranged with the first sensing element 51 in the Y-axis direction. For example, the multiple first sensing elements 51 are connected in series to each other. For example, the multiple second sensing elements 52 are connected in series to each other. In the embodiment, the number of the first sensing elements 51 is arbitrary. The number of the second sensing elements 52 is arbitrary.

The film portion 70d is held by a holder 70s. The film portion 70d includes an outer edge 70r. The holder 70s holds the outer edge 70r. For example, a substrate that is used to form the film portion 70d and the holder 70s is provided. The substrate is, for example, a silicon substrate. A hollow 70h is provided in the substrate by removing a portion of the substrate (referring to FIG. 1B). The thin portion of the substrate is used as the film portion 70d. The thick portion of the substrate is used as the holder 70s.

As shown in FIG. 1B, the first sensing element 51 includes a first magnetic layer 11a of a first material, a first opposing magnetic layer 11b, and a first intermediate layer 11c. The first intermediate layer 11c is provided between the first magnetic layer 11a and the first opposing magnetic layer 11b. The first opposing magnetic layer 11b is separated from the first magnetic layer 11a substantially along the Z-axis direction. In the example, the first opposing magnetic layer 11b is provided between the first magnetic layer 11a and the film portion 70d. In the embodiment, the first magnetic layer 11a may be disposed between the first opposing magnetic layer 11b and the film portion 70d.

The second sensing element 52 includes a second magnetic layer 12a of a second material, a second opposing magnetic layer 12b, and a second intermediate layer 12c. The second intermediate layer 12c is provided between the second magnetic layer 12a and the second opposing magnetic layer 12b. The second opposing magnetic layer 12b is separated from the second magnetic layer 12a substantially along the Z-axis direction. In the example, the second opposing magnetic layer 12b is provided between the second magnetic layer 12a and the film portion 70d. In the embodiment, the second magnetic layer 12a may be disposed between the second opposing magnetic layer 12b and the film portion 70d.

The magnetization (a first magnetization) of the first magnetic layer 11a changes according to the deformation of the film portion 70d. The magnetization (a second magnetization) of the second magnetic layer 12a changes according to the deformation of the film portion 70d. The first magnetic layer 11a is, for example, a free magnetic layer. The second magnetic layer 12a is, for example, a free magnetic layer.

For example, the magnetization of the first opposing magnetic layer 11b does not change easily compared to the first magnetization of the first magnetic layer 11a. The first opposing magnetic layer 11b is, for example, a fixed magnetic layer (e.g., a reference layer). For example, the magnetization of the second opposing magnetic layer 12b does not change easily compared to the second magnetization of the second magnetic layer 12a. The second opposing magnetic layer 12b is, for example, a fixed magnetic layer (e.g., a reference layer).

For example, pressure (the pressure to be sensed) is applied to the film portion 70d. Thereby, strain is generated in the magnetic layers of the sensing elements. The strain is, for example, an anisotropic strain. Due to the strain, the first magnetization of the first magnetic layer 11a and the second magnetization of the second magnetic layer 12a change. For example, the changes are based on an inverse magnetostrictive effect. Thereby, the angle between the direction of the first magnetization of the first magnetic layer 11a and the direction of the magnetization of the first opposing magnetic layer 11b changes. Thereby, the resistance between the first magnetic layer 11a and the first opposing magnetic layer 11b changes. On the other hand, the angle between the direction of the second magnetization of the second magnetic layer 12a and the direction of the magnetization of the second opposing magnetic layer 12b changes. Thereby, the resistance between the second magnetic layer 12a and the second opposing magnetic layer 12b changes. For example, these changes of the resistances are based on a magnetoresistance effect (MR effect).

In other words, the resistance between the first magnetic layer 11a and the first opposing magnetic layer 11b changes according to the deformation of the film portion 70d. The angle between the direction of the second magnetization of the second magnetic layer 12a and the direction of the magnetization of the second opposing magnetic layer 12b changes. By sensing these changes of the resistances, the pressure applied to the film portion 70d is sensed. In other words, the pressure to be sensed is sensed.

In the embodiment, the magnetization of the first opposing magnetic layer 11b may change according to the deformation of the film portion 70d. In such a case as well, the angle between the direction of the first magnetization of the first magnetic layer 11a and the direction of the magnetization of the first opposing magnetic layer 11b changes. In the embodiment, the magnetization of the second opposing magnetic layer 12b may change according to the deformation of the film portion 70d. In such a case as well, the angle between the direction of the second magnetization of the second magnetic layer 12a and the direction of the magnetization of the second opposing magnetic layer 12b changes.

For example, the change of the resistance is sensed by causing a current to flow in the sensing element.

For example, a first electrode 58a and a second electrode 58b are provided as illustrated in FIG. 1B. For example, the first magnetic layer 11a, the first opposing magnetic layer 11b, and the first intermediate layer 11c are disposed between the first electrode 58a and the second electrode 58b. The resistance of the first sensing element 51 is sensed by applying a voltage between the first electrode 58a and the second electrode 58b.

For example, a third electrode 58c and a fourth electrode 58d are provided as illustrated in FIG. 1D. For example, the second magnetic layer 12a, the second opposing magnetic layer 12b, and the second intermediate layer 12c are disposed between the third electrode 58c and the fourth electrode 58d. The resistance of the second sensing element 52 is sensed by applying a voltage between the third electrode 58c and the fourth electrode 58d.

In the example as illustrated in FIG. 1B, an insulating layer 58i is provided between the first electrode 58a and the film portion 70d. For example, the insulating layer 58i also is provided between the first electrode 58a and the second electrode 58b. For example, the insulating layer 58i also is provided between the third electrode 58c and the fourth electrode 58d. The electrodes are electrically insulated from each other by the insulating layer 58i.

As shown in FIG. 1C, the pressure sensor 110 may further include a processor 68 (e.g., a processing circuit). The processor 68 is electrically connected to the first sensing element 51 and the second sensing element 52. For example, the processor 68 is electrically connected to the first electrode 58a, the second electrode 58b, the third electrode 58c, and the fourth electrode 58d. The processor 68 outputs a signal corresponding to the signal obtained from the first sensing element 51 (the signal generated by the first sensing element 51). The processor 68 outputs a signal corresponding to the signal obtained from the second sensing element 52 (the signal generated by the second sensing element 52). The processor 68 outputs signals corresponding to the changes of the resistances generated in the sensing elements. The signals obtained by the processor 68 correspond to the pressure to be sensed.

In the example as shown in FIG. 1C, the film portion 70d (the outer edge 70r) is substantially a polygon (a quadrilateral, specifically, a rectangle). The outer edge 70r of the film portion 70d includes a first side 70s1, a second side 70s2, a third side 70s3, and a fourth side 70s4.

Various configurations are applicable to the film portion 70d (the outer edge 70r). For example, the film portion 70d (the outer edge 70r) may have a substantially perfect circle configuration, a flattened circular configuration (including an elliptical configuration), a substantially square configuration, or a rectangular configuration. For example, in the case where the film portion 70d (the outer edge 70r) is a substantially square configuration or a substantially rectangular configuration, the portions at the four corners (the corners) may have curved configurations.

The first side 70s1 extends in a first direction (in the example, the X-axis direction). The second side 70s2 is separated from the first side 70s1 in a second direction. The second direction intersects the first direction. In the example, the second direction is the Y-axis direction. The second side 70s2 extends in the first direction (the X-axis direction). The third side 70s3 extends in the second direction (the Y-axis direction). The fourth side 70s4 is separated from the third side 70s3 in the first direction (the X-axis direction) and extends in the second direction (the Y-axis direction).

In the example, the distance along the first direction between the third side 70s3 and the fourth side 70s4 is longer than the distance along the second direction between the first side 70s1 and the second side 70s2. The film portion 70d is substantially a rectangle; and the first side 70s1 and the second side 70s2 are the long sides. The third side 70s3 and the fourth side 70s4 are the short sides.

In the embodiment as illustrated in FIG. 1C, curved portions may be provided between the sides at the outer edge 70r. For example, the corners of the film portion 70d (the outer edge 70r) have curved configurations. Thereby, for example, the strength of the film portion 70d increases.

When stress is applied to the film portion 70d, a large strain (an anisotropic strain) is generated at the vicinity of the outer edge 70r of the film portion 70d. By disposing the sensing elements at the vicinity of the outer edge 70r of the film portion 70d, the large strain is applied to the sensing elements; and high sensitivity is obtained. In particular, in the case where one length of the film portion 70d is longer than the length in the other direction (i.e., in the case where the configuration is anisotropic), a particularly large strain is generated in the portion of the outer edge 70r along the major axis. Therefore, particularly high sensitivity is obtained by disposing the sensing elements at the portion along the long side of the outer edge 70r.

In the example, the multiple first sensing elements 51 are arranged along the first side 70s1. The multiple second sensing elements 52 are arranged along the second side 70s2. The region where the anisotropic strain is generated at the end portion vicinity on the minor axis side of the film portion 70d is wider for the case where one length of the film portion 70d is longer than the other length of the film portion 70d (the case where the configuration is anisotropic) than for the case where the film portion 70d has an isotropic configuration.

An anisotropic strain having a large absolute value is generated in a wider region for the end portion on the minor axis side of the film portion 70d having the anisotropic configuration than for the end portion of the film portion 70d having the isotropic configuration. More sensing elements can be disposed in the film portion 70d having the anisotropic configuration than in the film portion 70d having the isotropic configuration. The sensing elements that are disposed are sensing elements in which the changes of the electrical resistances are similar (e.g., have the same polarity) for the pressure. Thereby, a highly-sensitive pressure sensor can be provided.

The SN ratio can be improved by connecting the multiple sensing elements in series. In the embodiment, the multiple sensing elements that obtain electrical signals of the same polarity when the pressure is applied can be disposed. Thereby, the SN ratio improves.

In the embodiment, for example, a number N and the bias voltage of sensing elements connected in series are set so that an appropriate voltage range is obtained. For example, it is favorable for the voltage when the multiple sensing elements are connected electrically in series to be not less than 1 V and not more than 10 V. For example, in the case where the bias voltage applied to one sensing element is 50 mV, it is favorable for the number N of sensing elements connected in series to be not less than 20 and not more than 200. In the case where the bias voltage applied to one sensing element is 150 mV, it is favorable for the number N of sensing elements connected in series to be not less than 7 and not more than 66.

In the embodiment, the second material of the second magnetic layer 12a is different from the first material of the first magnetic layer 11a. Thereby, the sensitivity of the second sensing element 52 including the second magnetic layer 12a is different from the sensitivity of the first sensing element 51 including the first magnetic layer 11a. The sensitivity is a gauge factor described below.

For example, the composition of the second magnetic layer 12a is different from the composition of the first magnetic layer 11a. For example, the first magnetic layer 11a includes at least one of Fe, Co, or Ni with a first concentration. The second magnetic layer 12a includes the at least one of Fe, Co, or Ni recited above with a second concentration. The second concentration is different from the first concentration.

For example, the concentration (the composition ratio) of Fe of the second magnetic layer 12a is different from the concentration (the composition ratio) of Fe of the first magnetic layer 11a. For example, the concentration (the composition ratio) of Co of the second magnetic layer 12a is different from the concentration (the composition ratio) of Co of the first magnetic layer 11a. For example, the concentration (the composition ratio) of Ni of the second magnetic layer 12a is different from the concentration (the composition ratio) of Ni of the first magnetic layer 11a.

For example, the first magnetic layer 11a includes Fe; and the second magnetic layer 12a includes Fe. In such a case, the concentration (the composition ratio) of Fe of the second magnetic layer 12a is different from the concentration (the composition ratio) of Fe of the first magnetic layer 11a. For example, the composition ratio of Fe of the first magnetic layer 11a is not less than 60 at. % (atomic percent) and not more than 100 at. %. For example, the composition ratio of Fe of the second magnetic layer 12a is not less than 0 at. % but less than 60 at. %.

For example, the concentration of B (boron) may be different between the first magnetic layer 11a and the second magnetic layer 12a. Thereby, the sensitivity of the second sensing element 52 is different from the sensitivity of the first sensing element 51. For example, the composition ratio of B of the first magnetic layer 11a is not less than 10 at. % and not more than 30 at. %. For example, the composition ratio of B of the second magnetic layer 12a is not less than 0 at. % but less than 10 at. %.

For example, the first magnetic layer 11a includes B and at least one of Fe, Co, or Ni. The second magnetic layer 12a includes at least one of Fe, Co, or Ni but does not include B. In such a case, the sensitivity of the second sensing element 52 is lower than the sensitivity of the first sensing element 51.

For example, the first magnetic layer 11a includes B and at least one of Fe, Co, or Ni. The second magnetic layer 12a includes B and at least one of Fe, Co, or Ni. The concentration (the composition ratio) of B included in the second magnetic layer 12a is lower than the concentration (the composition ratio) of B included in the first magnetic layer 11a. For example, the composition ratio of Fe of the first magnetic layer 11a is not less than 60 at. % (atomic percent) and not more than 100 at. %. For example, the composition ratio of Fe of the second magnetic layer 12a is not less than 0 at. % but less than 60 at. %. For example, the composition ratio of B of the first magnetic layer 11a is not less than 10 at. % and not more than 30 at. %. For example, the composition ratio of B of the second magnetic layer 12a is not less than 0 at. % but less than 10 at. %. In such a case, the sensitivity of the second sensing element 52 is lower than the sensitivity of the first sensing element 51.

For example, the first magnetic layer 11a includes $Co_{40}Fe_{40}B_{20}$. For example, the second magnetic layer 12a includes $Co_{50}Fe_{50}$.

For example, the first magnetic layer 11a includes $Fe_{80}B_{20}$. For example, the second magnetic layer 12a includes $Co_{40}Fe_{40}B_{20}$.

For example, the compositions of these magnetic layers are determined by a combination of the analysis methods of cross-section TEM (Transmission Electron Microscope) and EDX (Energy Dispersive X-ray Spectroscopy). For example, the compositions of these magnetic layers are determined by a combination of the analysis methods of cross-section TEM and EELS (Electron Energy-Loss Spectroscopy). For example, the compositions of these magnetic layers are determined by an analysis method such as SIMS (Secondary Ion Mass Spectrometry), etc.

For example, the crystallinity may be different between the first magnetic layer 11a and the second magnetic layer 12a. For example, the first magnetic layer 11a includes an amorphous region. The second magnetic layer 12a includes a crystal region. For example, the second magnetic layer 12a does not include an amorphous region. For example, the amount of the amorphous region (e.g., the size of the amorphous region per unit cross-sectional area) of the second magnetic layer 12a is less than the amount of the amorphous region (e.g., the size of the amorphous region per unit cross-sectional area) of the first magnetic layer 11a. For example, the first magnetic layer 11a substantially may not include a crystal region.

The crystallinity of these magnetic layers is determined by an analysis method such as cross-section TEM (Transmission Electron Microscope), etc.

Examples of the first magnetic layer 11a included in the first sensing element 51 and the second magnetic layer 12a included in the second sensing element 52 will now be described.

FIG. 2A to FIG. 2D are schematic views illustrating the pressure sensor according to the first embodiment.

FIG. 2A and FIG. 26 correspond to a first configuration S01. FIG. 2C and FIG. 2D correspond to a second configuration S02.

FIG. 2A and FIG. 2C show examples of depth profiles of the elements of samples by electron energy-loss spectroscopy (EELS). In these figures, the horizontal axis is a detection strength Int of the elements (arbitrary units). The vertical axis is a depth Dp (nm). For example, the depth Dp corresponds to the distance in the Z-axis direction. The depth profiles relating to iron, boron, and oxygen are shown in FIG. 2A and FIG. 2C. FIG. 2B and FIG. 2D are cross-section transmission electron microscope (cross-section TEM) photographs of the samples.

The sample of the first configuration S01 has the following configuration. A pinning layer ($Ir_{22}Mn_{78}$, 7 nm) is provided on a foundation layer ((Ta, 1 nm)/(Ru, 2 nm)). A fixed magnetic layer ($Co_{75}Fe_{25}$, 2.5 nm) is provided on the pinning layer. A magnetic coupling layer (Ru, 0.9 nm) is provided on the fixed magnetic layer. A fixed magnetic layer ($Co_{40}Fe_{40}B_{20}$, 3 nm) is provided on the magnetic coupling layer. An intermediate layer (Mg—O, 1.6 nm) is provided on the fixed magnetic layer. A magnetic layer ($Co_{40}Fe_{40}B_{20}$, 4 nm) is provided on the intermediate layer. A functional layer (Mg—O, 1.5 nm) is provided on the magnetic layer. A capping layer ((Cu, 1 nm)/(Ta, 20 nm)/(Ru, 50 nm)) is provided on the functional layer.

The magnetic layer ($Co_{40}Fe_{40}B_{20}$, 4 nm) corresponds to the first magnetic layer 11a. The intermediate layer corresponds to the first intermediate layer 11c. The fixed magnetic layer ($Co_{40}Fe_{40}B_{20}$, 3 nm) corresponds to the first opposing magnetic layer 11b.

On the other hand, the sample of the second configuration S02 is the sample of the first configuration S01 recited above without the functional layer being provided. The magnetic layer ($Co_{40}Fe_{40}B_{20}$, 4 nm) corresponds to the second magnetic layer 12a. The intermediate layer corresponds to the second intermediate layer 12c. The fixed magnetic layer ($Co_{40}Fe_{40}B_{20}$, 3 nm) corresponds to the second opposing magnetic layer 12b.

It can be seen from FIG. 2A that the concentration of boron is high in the first magnetic layer 11a (the Co—Fe—B layer) in the first configuration S01. It can be seen from FIG. 2C that the concentration of boron is low in the second magnetic layer 12a (the Co—Fe—B layer) in the second configuration S02. It is considered that the concentration of boron of the second magnetic layer 12a decreases due to the boron diffusing to the capping layer side.

The crystallization progresses more for the $Co_{40}Fe_{40}B_{20}$ layer of the second configuration S02 in which the functional layer is not provided than for the $Co_{40}Fe_{40}B_{20}$ layer of the first configuration S01. In the first configuration S01, the $Co_{40}Fe_{40}B_{20}$ layer has an amorphous structure. The crystallization progresses in the second configuration S02 in which the functional layer is not provided. It is considered that this is because, in the second configuration S02, the boron content of the second magnetic layer 12a decreases due to the diffusion of the boron.

Thus, the concentration (the composition ratio) of B included in the second magnetic layer 12a is lower than the concentration (the composition ratio) of B included in the first magnetic layer 11a. Or, the second magnetic layer 12a does not include B.

Figure 3B:
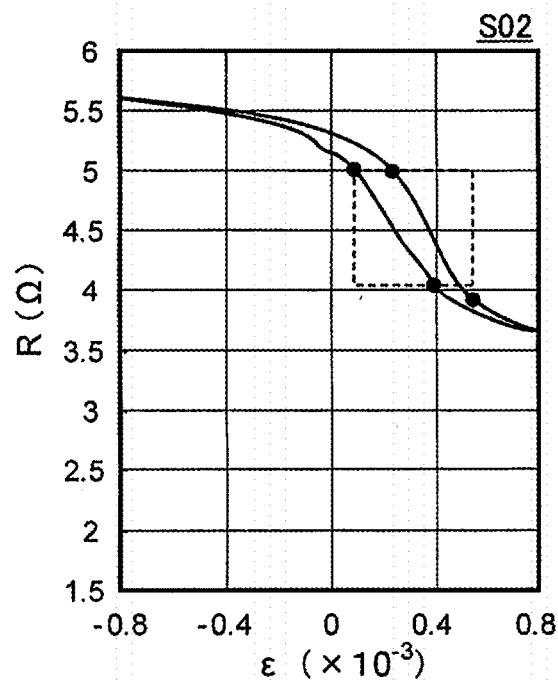

FIG. 3A and FIG. 3B are schematic views illustrating the pressure sensor according to the first embodiment.

These figures are graphs of characteristics of the sensing elements. FIG. 3A corresponds to the first configuration S01; and FIG. 3B corresponds to the second configuration S02. These figures show an electrical resistance R of the sensing element when a strain ε is changed. The strain 6 is changed continuously in the range between $-0.8 \times 10^{-3}$ and $0.8 \times 10^{-3}$. The horizontal axis is the strain ε. The vertical axis is the electrical resistance R. The change of the strain ε includes both the change from $-0.8 \times 10^{-3}$ toward $0.8 \times 10^{-3}$ and the change from $0.8 \times 10^{-3}$ toward $-0.8 \times 10^{-3}$. The gauge factor is calculated from these figures.

A gauge factor GF is expressed by GF=(dR/R)/dε. The gauge factor of the first configuration S01 is calculated to be 4027. The gauge factor of the second configuration S02 is calculated to be 895.

Thus, the concentration of B is different between the first configuration S01 and the second configuration S02; and as a result, different gauge factors are obtained.

In the embodiment, for example, the first configuration S01 recited above is applied as the first magnetic layer 11a of the first sensing element 51. On the other hand, for example, the second configuration S02 recited above is applied as the second magnetic layer 12a of the second sensing element 52. Thereby, the gauge factor of the second sensing element 52 is modified from the gauge factor of the first sensing element 51.

FIG. 4A to FIG. 4D are graphs of characteristics of the pressure sensor according to the first embodiment.

Figure 4A:
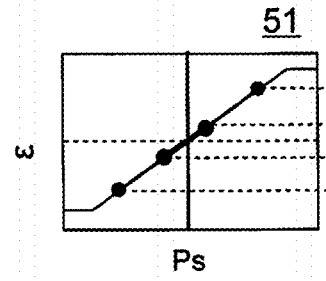
FIG. 4A to FIG. 4D are graphs of characteristics of the pressure sensor according to the first embodiment.
Figure 4B:
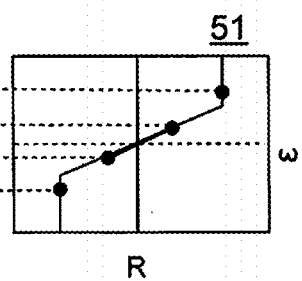
Figure 4C:
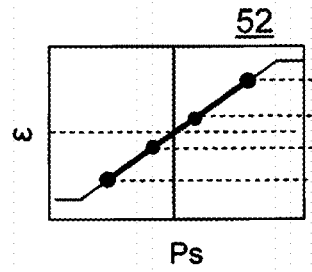
Figure 4D:
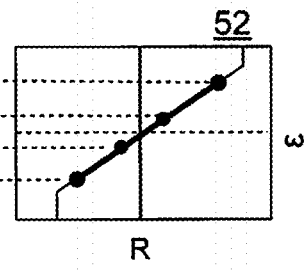

FIG. 4A and FIG. 4B correspond to the first sensing element 51. FIG. 4C and FIG. 4D correspond to the second sensing element 52. In FIG. 4A and FIG. 4C, the horizontal axis is a pressure Ps; and the vertical axis is the strain ε. In FIG. 4B and FIG. 4D, the horizontal axis is the electrical resistance R; and the vertical axis is the strain ε.

As shown in FIG. 4A and FIG. 4B, for the first sensing element 51 having the high gauge factor, the electrical resistance R changes according to the pressure Ps when a small pressure Ps is applied. Because the gauge factor is high, the sensitivity of the electrical resistance R for the pressure Ps is high. For the first sensing element 51, when a large pressure Ps is applied, the electrical resistance R is in the saturated state; and a change of the electrical resistance R corresponding to the pressure Ps is not obtained.

On the other hand, as shown in FIG. 4C and FIG. 4D, for the second sensing element 52 having the low gauge factor, the electrical resistance R changes according to the pressure Ps when a large pressure Ps is applied. When a small pressure Ps is applied, the sensitivity of the electrical resistance R for the pressure Ps is low compared to that of the first sensing element 51.

Such a first sensing element 51 and second sensing element 52 are included in the embodiment. Thereby, for example, the small pressure is sensed using the first sensing element 51. The large pressure is sensed using the second sensing element 52. Thereby, the small pressure and the large pressure can be sensed. In other words, a pressure sensor in which the dynamic range can be enlarged can be provided. The sensitivity when sensing the small pressure by the first sensing element 51 is high. In other words, a high sensitivity and a wide dynamic range are obtained.

For example, the pressure sensor 110 is applied to a microphone. For example, small sounds are sensed by the first sensing element 51; and large sounds are sensed by the second sensing element 52. The sound can be sensed with high sensitivity and a wide dynamic range.

The strain (the anisotropic strain) that is generated when the pressure is applied is different between positions in the surface of the film portion 70d. The first sensing element 51 and the second sensing element 52 may be disposed in regions of the film portion 70d in which similar strain is generated. In the embodiment, the first sensing element 51 and the second sensing element 52 have mutually-different gauge factors. Therefore, the changes of the electrical resistances R that are obtained are different even in the case where these sensing elements are disposed in the regions of the film portion 70d in which similar strain is generated.

In the embodiment, these sensing elements 51 may be disposed in a region where a large strain is obtained. Thereby, sensing with high sensitivity is possible.

For example, the first sensing element 51 is most proximal to a first portion of the outer edge 70r of the film portion 70d. The first portion is, for example, the first side 70s1. The second sensing element 52 is most proximal to a second portion of the outer edge 70r. The second portion is the second side 70s2. A first spacing between the first sensing element 51 and the first portion is substantially equal to a second spacing between the second sensing element 52 and the second portion. The difference between the first spacing and the second spacing is, for example, not more than 0.2 times the first spacing.

As described above, a large strain (an anisotropic strain) is obtained at the vicinity of the outer edge 70r of the film portion 70d. By disposing the sensing elements in regions in the vicinity of the outer edge 70r, a high sensitivity is obtained. Even in the case where the sensing elements having mutually-different gauge factors are disposed in similar regions, a wide dynamic range is obtained.

For example, these sensing elements may be stacked. For example, at least a portion of the second sensing element 52 may overlap the first sensing element 51 along a direction (the Z-axis direction) from the film portion 70d toward the first sensing element 51. In such a case as well, a wide dynamic range is obtained.

In the embodiment, for example, one of the signal obtained from the first sensing element 51 or the signal obtained from the second sensing element 52 may be output as the sense signal. For example, the selection of the signal is performed by the processor 68. In other words, the pressure sensor 110 further includes the processor 68 that is connected to the first sensing element 51 and the second sensing element 52. The processor 68 implements a first operation of outputting a first output signal corresponding to a first signal obtained from the first sensing element 51, and a second operation of outputting a second output signal corresponding to a second signal obtained from the second sensing element 52.

For example, the processor 68 implements the first operation recited above when a first amplitude of the first signal is wider than a second amplitude of the second signal. The second operation is implemented when the second amplitude is wider than the first amplitude.

For example, the processor 68 implements the first operation recited above when the first amplitude of the first signal is not more than a threshold. The second operation is implemented when the first amplitude exceeds the threshold.

Thus, the pressure sensor 110 includes the deformable film portion 70d, the first sensing element 51, the second sensing element 52, and the processor 68. The first sensing element 51 is fixed to the film portion 70d and includes the first magnetic layer 11a, the first opposing magnetic layer 11b, and the first intermediate layer 11c provided between the first magnetic layer 11a and the first opposing magnetic layer 11b. The second sensing element 52 is fixed to the film portion 70d and includes the second magnetic layer 12a, the second opposing magnetic layer 12b, and the second intermediate layer 12c provided between the second magnetic layer 12a and the second opposing magnetic layer 12b. The processor 68 is connected to the first sensing element 51 and the second sensing element 52. The processor 68 implements the first operation of outputting the first output signal corresponding to the first signal obtained from the first sensing element 51, and the second operation of outputting the second output signal corresponding to the second signal obtained from the second sensing element 52.

By the operations of the processor 68, a pressure sensor in which the dynamic range can be enlarged can be provided.

Second Embodiment

FIG. 5 is a schematic plan view illustrating a pressure sensor according to a second embodiment.

As shown in FIG. 5, the pressure sensor 120 according to the embodiment includes the film portion 70*d*, the first sensing element 51, the second sensing element 52, a third magnetic layer 43, and a fourth magnetic layer 44. The film portion 70*d* is deformable. The first sensing element 51 is fixed to the film portion 70*d*. The first sensing element 51 includes the first magnetic layer 11*a*, the first opposing magnetic layer 11*b*, and the first intermediate layer 11*c* provided between the first magnetic layer 11*a* and the first opposing magnetic layer 11*b* (referring to FIG. 1B). The second sensing element 52 is fixed to the film portion 70*d*. The second sensing element 52 includes the second magnetic layer 12*a*, the second opposing magnetic layer 12*b*, and the second intermediate layer 12*c* provided between the second magnetic layer 12*a* and the second opposing magnetic layer 12*b* (referring to FIG. 1D).

The third magnetic layer 43 includes at least one selected from the group consisting of a first alloy including Co and Pt, a second alloy including Fe and Pt, a third alloy including Co and Pd, and a fourth alloy including Fe and Pd.

The fourth magnetic layer 44 includes at least one selected from the group consisting of a sixth alloy including Co and Pt, a seventh alloy including Fe and Pt, an eighth alloy including Co and Pd, and a ninth alloy including Fe and Pd.

In the example, multiple third magnetic layers 43 (a magnetic layer 43*a* and a magnetic layer 43*b*) are provided. The first sensing element 51 is disposed between these magnetic layers.

In the example, multiple fourth magnetic layers 44 (a magnetic layer 44*a* and a magnetic layer 44*b*) are provided. The second sensing element 52 is disposed between these magnetic layers.

In the pressure sensor 120, the configurations described in reference to the first embodiment are applicable to the film portion 70*d*, the first sensing element 51, and the second sensing element 52. However, in the second embodiment, the materials of the first sensing element 51, etc., may be the same as or different from the materials of the second sensing element 52, etc. The processor 68 may be provided in the pressure sensor 120. The portions of the pressure sensor 120 that are different from those of the pressure sensor 110 will now be described.

In the second embodiment, a characteristic (e.g., the gauge factor) of the first sensing element 51 is different from a characteristic (e.g., the gauge factor) of the second sensing element 52 due to the third magnetic layers 43 and the fourth magnetic layers 44.

For example, the third magnetic layers 43 apply a magnetic field bias to the first sensing element 51. The fourth magnetic layers 44 apply a magnetic field bias to the second sensing element 52. These magnetizing biases are different from each other.

The third magnetic layers 43 are disposed proximally to the first magnetic layer 11*a*. The fourth magnetic layers 44 are disposed proximally to the second magnetic layer 12*a*. For example, a first distance d1 between the first magnetic layer 11*a* and the third magnetic layer 43 is shorter than a distance d3 between the first magnetic layer 11*a* and the fourth magnetic layer 44. A second distance d2 between the second magnetic layer 12*a* and the fourth magnetic layer 44 is shorter than a distance d4 between the second magnetic layer 12*a* and the third magnetic layer 43.

In such a case, at least one of the thickness of the layer, the length of the layer, the width of the layer, the distance between the free magnetic layers, the composition, or the magnetization direction is different between the third magnetic layer 43 and the fourth magnetic layer 44.

FIG. 6A to FIG. 6D are schematic perspective views illustrating the pressure sensor according to the second embodiment.

In the example shown in FIG. 6A, the third magnetic layer 43 is arranged with the first sensing element 51 (the first magnetic layer 11*a*) in a direction intersecting the Z-axis direction. In the example shown in FIG. 6B, the fourth magnetic layer 44 is arranged with the second sensing element 52 (the second magnetic layer 12*a*) in a direction intersecting the Z-axis direction.

As shown in FIG. 6A, for example, the third magnetic layer 43 has a first length L1, a second length L2, a third length L3, a first distance d1, and a third magnetization direction 43M. The third magnetic layer 43 further has a first composition. The first length L1 is the length (the thickness) of the third magnetic layer 43 along the first direction. The first direction corresponds to the Z-axis direction from the film portion 70*d* toward the first sensing element 51. The second length L2 is the length of the third magnetic layer 43 along the second direction. The second direction is perpendicular to the first direction. In the example, the second direction is the X-axis direction. The third length L3 is the length (the width) of the third magnetic layer 43 along the third direction. The third direction is perpendicular to the first direction and perpendicular to the second direction. The first distance d1 is the distance between the first magnetic layer 11*a* and the third magnetic layer 43. The third magnetization direction 43M is the direction of the magnetization of the third magnetic layer 43.

As shown in FIG. 6B, for example, the fourth magnetic layer 44 has a fourth length L4, a fifth length L5, a sixth length L6, the second distance d2, and a fourth magnetization direction 44M. The fourth magnetic layer 44 further has a second composition. The fourth length L4 is the length (the thickness) of the fourth magnetic layer 44 along the first direction. The fifth length L5 is the length of the fourth magnetic layer 44 along the second direction. The sixth length L6 is the length (the width) of the fourth magnetic layer 44 along the third direction. The second distance d2 is the distance between the second magnetic layer 12*a* and the fourth magnetic layer 44. The fourth magnetization direction 44M is the direction of the magnetization of the fourth magnetic layer 44.

As shown in FIG. 6A and FIG. 6B, the fourth length L4 is different from the first length L1. The fifth length L5 is different from the second length L2. The sixth length L6 is different from the third length L3. The second distance d2 is different from the first distance d1. The fourth magnetization direction 44M is different from the third magnetization direction 43M. The second composition of the fourth magnetic layer 44 may be different from the first composition of the third magnetic layer 43.

In the example shown in FIG. 6C, at least a portion of the third magnetic layer 43 is arranged with the first sensing element 51 (the first magnetic layer 11*a*) in the Z-axis direction. In the example shown in FIG. 6D, at least a portion of the fourth magnetic layer 44 is arranged with the second sensing element 52 (the second magnetic layer 12a) in the Z-axis direction.

As shown in FIG. 6C and FIG. 6D, the fourth length L4 is different from the first length L1. The fifth length L5 is different from the second length L2. The sixth length L6 is different from the third length L3. The second distance d2 is different from the first distance d1. The fourth magnetization direction 44M is different from the third magnetization direction 43M. The second composition of the fourth magnetic layer 44 may be different from the first composition of the third magnetic layer 43.

Thus, in the embodiment, the fourth magnetic layer 44 has at least one of the fourth length L4 that is different from the first length L1, the fifth length L5 that is different from the second length L2, the sixth length L6 that is different from the third length L3, the second distance d2 that is different from the first distance d1, the second composition that is different from the first composition, or the fourth magnetization direction 44M that is different from the third magnetization direction 43M.

Thereby, the characteristic (e.g., the gauge factor) of the second sensing element 52 is different from the characteristic (e.g., the gauge factor) of the first sensing element 51. For example, the gauge factor of the second sensing element 52 is lower than the gauge factor of the first sensing element 51.

By using such multiple sensing elements, a pressure sensor in which the dynamic range can be enlarged can be provided.

In the pressure sensor 120, for example, Co—Pt, Fe—Pt, Co—Pd, Fe—Pd, or the like is included in at least one of the third magnetic layer 43 or the fourth magnetic layer 44. The magnetic anisotropy and the coercivity are relatively high for these materials. These materials are, for example, hard magnetic materials (hard ferromagnetic materials).

At least one of the third magnetic layer 43 or the fourth magnetic layer 44 may include an alloy in which an added element is further added to Co—Pt, Fe—Pt, Co—Pd, or Fe—Pd.

At least one of the third magnetic layer 43 or the fourth magnetic layer 44 includes, for example, at least one of CoPt (the proportion of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), or FePt (the proportion of Pt being not less than 40 at. % and not more than 60 at. %).

For example, the third magnetic layer 43 includes Fe—Pt (the proportion of Fe being not less than 30 at. % and not more than 70 at. %). The fourth magnetic layer 44 includes CoPt (the proportion of Co being not less than 50 at. % and not more than 85 at. %). In such a case, for example, the magnetic field bias that is applied from the fourth magnetic layer 44 to the second magnetic layer 12a is lower than the magnetic field bias applied from the third magnetic layer 43 to the first magnetic layer 11a. The gauge factor of the second sensing element 52 is higher than the gauge factor of the first sensing element 51.

For example, the first alloy that is included in the fourth magnetic layer 44 includes $(Co_xPt_{100-x})_{100-y}Cr_y$. x is not less than 50 at. % and not more than 85 at. %. y is not less than 0 at. % and not more than 40 at. %.

As described below, the third magnetic layer 43 and the fourth magnetic layer 44 each may have a configuration of stacked films.

FIG. 7A and FIG. 7B are schematic perspective views illustrating portions of another pressure sensor according to the second embodiment.

The pressure sensor 121 also includes the film portion 70d, the first sensing element 51, the second sensing element 52, the third magnetic layer 43, and the fourth magnetic layer 44. FIG. 7A and FIG. 7B show the third magnetic layer 43 and the fourth magnetic layer 44 of the pressure sensor 121.

As shown in FIG. 7A, the third magnetic layer 43 includes a first film 43p and a second film 43q. As shown in FIG. 7B, the fourth magnetic layer 44 includes a third film 44p and a fourth film 44q. Otherwise, the configuration of the pressure sensor 121 is similar to that of the pressure sensor 120 or the pressure sensor 110; and a description is therefore omitted. These films will now be described.

In the third magnetic layer 43, the first film 43p includes at least one of Fe, Co, or Ni. The second film 43q includes at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O.

In the fourth magnetic layer 44, the third film 44p includes at least one of Fe, Co, or Ni. The fourth film 44q includes at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O.

For example, the second film 43q overlaps the first film 43p in the first direction (the Z-axis direction). The fourth film 44q overlaps the third film 44p in the first direction.

For example, the third magnetic layer 43 that has such a configuration can apply a magnetic field bias to the first magnetic layer 11a. For example, the fourth magnetic layer 44 can apply a magnetic field bias to the second magnetic layer 12a.

Mutually-different configurations are applied to the third magnetic layer 43 and the fourth magnetic layer 44. For example, the fourth magnetic layer 44 has at least one of the fourth length L4 along the first direction that is different from the first length L1 of the third magnetic layer 43, the fifth length L5 along the second direction that is different from the second length L2 of the third magnetic layer 43, the sixth length L6 along the third direction that is different from the third length L3 of the third magnetic layer 43, the second distance d2 between the second magnetic layer 12a and the fourth magnetic layer 44 that is different from the first distance d1 of the third magnetic layer 43, the second composition that is different from the first composition of the third magnetic layer 43, or the fourth magnetization direction that is different from the third magnetization direction of the third magnetic layer 43. In such a case as well, the first distance d1 is shorter than the distance d3 between the first magnetic layer 11a and the fourth magnetic layer 44. The second distance d2 is shorter than the distance d4 between the second magnetic layer 12a and the third magnetic layer 43.

By using the third magnetic layer 43 and the fourth magnetic layer 44 having such configurations, the characteristic (e.g., the gauge factor) of the second sensing element 52 is different from the characteristic (e.g., the gauge factor) of the first sensing element 51. According to the embodiment, a pressure sensor in which the dynamic range can be enlarged can be provided.

At least one of the first film 43p or the third film 44p may include an alloy including at least one material selected from the group consisting of Co, Fe, and Ni. For example, at least one of the first film 43p or the third film 44p may include a $Co_xFe_{100-x}$ alloy (x being not less than 0 at. % and not more than 100 at. %), a $Ni_xFe_{100-x}$ alloy (x being not less than 0 at. % and not more than 100 at. %), or a material in which a nonmagnetic element is added to these alloys. At least one of the first film 43p or the third film 44p may include $(Co_xFe_{100-x})_{100-y}B_y$ alloy (x being not less than 0 at. % and not more than 100 at. %, and y being not less than 0 at. % and not more than 30 at. %). By the at least one of the first film 43p or the third film 44p including an amorphous alloy of $(Co_xFe_{100-x})_{100-y}B_y$, the fluctuation of the characteristics between the strain sensing elements can be suppressed even in the case where the sizes of the sensing elements are small.

For example, the second film 43q provides the first film 43p with unidirectional anisotropy. For example, the second film 43q fixes the magnetization of the first film 43p. For example, the fourth film 44q provides the third film 44p with unidirectional anisotropy. For example, the fourth film 44q fixes the magnetization of the third film 44p. At least one of the first film 43p or the third film 44p includes, for example, an antiferromagnetic layer.

In the pressure sensor 121 as well, a pressure sensor in which the dynamic range can be enlarged can be provided.

Generally, in a spintronic strain sensor, the strain range in which a high gauge factor is obtained is limited. For example, the operational strain range (the sensible strain range) becomes narrow as the gauge factor increases. For example, in the case where a pressure sensor is applied to a microphone, high sound levels are outside the operational strain range of the sensor if the pressure sensor is designed to obtain a high gauge factor and a high NS ratio at normal sound levels. Therefore, the signal that corresponds to the sensed sound is distorted.

Conversely, in the pressure sensors according to the first and second embodiments recited above, for example, multiple sensing elements that have different strain sensitivities (gauge factors) are provided. High sensitivity and a wide dynamic range are provided. For example, spintronic strain sensors having different strain sensitivities are disposed on a diaphragm. In the case of normal sound levels, the sensing is performed by the sensing element having the high gauge factor; and in the case of high sound levels, the sensing is performed by the sensing element having the low gauge factor. Thereby, a high sensitivity and a wide dynamic range are obtained.

Examples of the sensing elements included in the first and second embodiments will now be described. In the following description, the notation "material A/material B" indicates a state in which a layer of material B is provided on a layer of material A.

FIG. 8 is a schematic perspective view illustrating a portion of the pressure sensor according to the embodiment.

In a sensing element 50A as shown in FIG. 8, a lower electrode 204, a foundation layer 205, a pinning layer 206, a second fixed magnetic layer 207, a magnetic coupling layer 208, a first fixed magnetic layer 209, an intermediate layer 203, a free magnetic layer 210, a capping layer 211, and an upper electrode 212 are arranged in this order. For example, the first fixed magnetic layer 209 corresponds to one of the first opposing magnetic layer 11b or the second opposing magnetic layer 12b. For example, the free magnetic layer 210 corresponds to one of the first magnetic layer 11a or the second magnetic layer 12a. The intermediate layer 203 corresponds to one of the first intermediate layer 11c or the second intermediate layer 12c. For example, the lower electrode 204 corresponds to the second electrode 58b. For example, the upper electrode 212 corresponds to the first electrode 58a. For example, the sensing element 50A is a bottom spin-valve type.

The foundation layer 205 includes, for example, a stacked film of tantalum and ruthenium (Ta/Ru). The thickness (the length in the Z-axis direction) of the Ta layer is, for example, 3 nanometers (nm). The thickness of the Ru layer is, for example, 2 nm. The pinning layer 206 includes, for example, an IrMn layer having a thickness of 7 nm. The second fixed magnetic layer 207 includes, for example, a $Co_{75}Fe_{25}$ layer having a thickness of 2.5 nm. The magnetic coupling layer 208 includes, for example, a Ru layer having a thickness of 0.9 nm. The first fixed magnetic layer 209 includes, for example, a $Co_{40}Fe_{40}B_{20}$ layer having a thickness of 3 nm. The intermediate layer 203 includes, for example, a MgO layer having a thickness of 1.6 nm. The free magnetic layer 210 includes, for example, $Co_{40}Fe_{40}B_{20}$ having a thickness of 4 nm. The capping layer 211 includes, for example, Ta/Ru. The thickness of the Ta layer is, for example, 1 nm. The thickness of the Ru layer is, for example, 5 nm.

The lower electrode 204 and the upper electrode 212 include, for example, at least one of aluminum (Al), an aluminum copper alloy (Al—Cu), copper (Cu), silver (Ag), or gold (Au). By using such a material having a relatively small electrical resistance as the lower electrode 204 and the upper electrode 212, the current can be caused to flow efficiently in the sensing element 50A. The lower electrode 204 and the upper electrode 212 include nonmagnetic materials.

The lower electrode 204 and the upper electrode 212 may include, for example, a foundation layer (not shown) for the lower electrode 204 and the upper electrode 212, a capping layer (not shown) for the lower electrode 204 and the upper electrode 212, and a layer of at least one of Al, Al—Cu, Cu, Ag, or Au provided between the foundation layer and the capping layer. For example, the lower electrode 204 and the upper electrode 212 include tantalum (Ta)/copper (Cu)/tantalum (Ta), etc. For example, by using Ta as the foundation layer for the lower electrode 204 and the upper electrode 212, the adhesion between the substrate (e.g., the film portion 70d) and the lower electrode 204 and between the substrate and the upper electrode 212 improves. Titanium (Ti), titanium nitride (TiN), etc., may be used as the foundation layer for the lower electrode 204 and the upper electrode 212.

By using Ta as the capping layer for the lower electrode 204 and the upper electrode 212, the oxidization of the copper (Cu), etc., under the capping layer is suppressed. Titanium (Ti), titanium nitride (TiN), etc., may be used as the capping layer for the lower electrode 204 and the upper electrode 212.

The foundation layer 205 includes, for example, a stacked structure including a buffer layer (not shown) and a seed layer (not shown). For example, the buffer layer relaxes the roughness of the front surfaces of the lower electrode 204, the film portion 70d, etc., and improves the crystallinity of the layers stacked on the buffer layer. For example, at least one selected from the group consisting of tantalum (Ta), titanium (Ti), vanadium (V), tungsten (W), zirconium (Zr), hafnium (Hf), and chrome (Cr) is used as the buffer layer. An alloy that includes at least one material selected from these materials may be used as the buffer layer.

It is favorable for the thickness of the buffer layer of the foundation layer 205 to be not less than 1 nm and not more than 10 nm. It is more favorable for the thickness of the buffer layer to be not less than 1 nm and not more than 5 nm. In the case where the thickness of the buffer layer is too thin, the buffering effect is lost. In the case where the thickness of the buffer layer is too thick, the thickness of the sensing element 50A becomes excessively thick. The seed layer is formed on the buffer layer; and, for example, the seed layer has a buffering effect. In such a case, the buffer layer may be omitted. The buffer layer includes, for example, a Ta layer having a thickness of 3 nm.

The seed layer of the foundation layer 205 controls the crystal orientation of the layers stacked on the seed layer. The seed layer controls the crystal grain size of the layers stacked on the seed layer. As the seed layer, a metal having a fcc structure (face-centered cubic structure), a hcp structure (hexagonal close-packed structure), a bcc structure (body-centered cubic structure), or the like is used.

For example, the crystal orientation of the spin-valve film on the seed layer can be set to the fcc (111) orientation by using, as the seed layer of the foundation layer 205, ruthenium (Ru) having a hcp structure, NiFe having a fcc structure, or Cu having a fcc structure. The seed layer includes, for example, a Cu layer having a thickness of 2 nm or a Ru layer having a thickness of 2 nm. To increase the crystal orientation of the layers formed on the seed layer, it is favorable for the thickness of the seed layer to be not less than 1 nm and not more than 5 nm. It is more favorable for the thickness of the seed layer to be not less than 1 nm and not more than 3 nm. Thereby, the function as a seed layer that improves the crystal orientation is realized sufficiently.

On the other hand, for example, the seed layer may be omitted in the case where it is unnecessary for the layers formed on the seed layer to have a crystal orientation (e.g., in the case where an amorphous free magnetic layer is formed, etc.). For example, a Ru layer having a thickness of 2 nm is used as the seed layer.

For example, the pinning layer 206 provides unidirectional anisotropy to the second fixed magnetic layer 207 (the ferromagnetic layer) formed on the pinning layer 206 and fixes the magnetization of the second fixed magnetic layer 207. The pinning layer 206 includes, for example, an antiferromagnetic layer. The pinning layer 206 includes, for example, at least one selected from the group consisting of Ir—Mn, Pt—Mn, Pd—Pt—Mn, Ru—Mn, Rh—Mn, Ru—Rh—Mn, Fe—Mn, t fixed to the film portion, the first sensing element including a first magnetic layer of a first material, a first opposing magnetic layer, and a first intermediate layer, the fir Rh—Mn, Ru—Rh—Mn, Fe—Mn, Ni—Mn, Cr—Mn—Pt, and Ni—O. The thickness of the pinning layer 206 is set appropriately. Thereby, for example, unidirectional anisotropy of sufficient strength is provided.

For example, heat treatment is performed while applying a magnetic field. Thereby, for example, the magnetization of the ferromagnetic layer contacting the pinning layer 206 is fixed. The magnetization of the ferromagnetic layer contacting the pinning layer 206 is fixed in the direction of the magnetic field applied in the heat treatment. For example, the heat treatment temperature (the annealing temperature) is not less than the magnetization pinning temperature of the antiferromagnetic material included in the pinning layer 206. In the case where an antiferromagnetic layer including Mn is used, there are cases where the MR ratio decreases due to the Mn diffusing into layers other than the pinning layer 206. It is desirable for the heat treatment temperature to be set to be not more than the temperature at which the diffusion of Mn occurs. The heat treatment temperature is, for example, not less than 200° C. and not more than 500° C. Favorably, the heat treatment temperature is, for example, not less than 250° C. and not more than 400° C.

In the case where PtMn or PdPtMn is used as the pinning layer 206, it is favorable for the thickness of the pinning layer 206 to be not less than 8 nm and not more than 20 nm. It is more favorable for the thickness of the pinning layer 206 to be not less than 10 nm and not more than 15 nm. In the case where IrMn is used as the pinning layer 206, unidirectional anisotropy can be provided using a thickness that is thinner than the case where PtMn is used as the pinning layer 206. In such a case, it is favorable for the thickness of the pinning layer 206 to be not less than 4 nm and not more than 18 nm. It is more favorable for the thickness of the pinning layer 206 to be not less than 5 nm and not more than 15 nm. The pinning layer 206 includes, for example, an $Ir_{22}Mn_{78}$ layer having a thickness of 7 nm.

A hard magnetic layer may be used as the pinning layer 206. For example, Co—Pt, Fe—Pt, Co—Pd, Fe—Pd, etc., may be used as the hard magnetic layer. For example, the magnetic anisotropy and the coercivity are relatively high for these materials. These materials are hard magnetic materials. An alloy in which an added element is further added to Co—Pt, Fe—Pt, Co—Pd, or Fe—Pd may be used as the pinning layer 206. For example, CoPt (the proportion of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), FePt (the proportion of Pt being not less than 40 at. % and not more than 60 at. %), etc., may be used.

The second fixed magnetic layer 207 includes, for example, a $Co_xFe_{100-x}$ alloy (x being not less than 0 at. % and not more than 100 at. %) or a $Ni_xFe_{100-x}$ alloy (x being not less than 0 at. % and not more than 100 at. %). These materials may include a material to which a nonmagnetic element is added. For example, at least one selected from the group consisting of Co, Fe, and Ni is used as the second fixed magnetic layer 207. An alloy that includes the at least one material selected from these materials may be used as the second fixed magnetic layer 207. Also, a $(Co_xFe_{100-x})_{100-y}B_y$ alloy (x being not less than 0 at. % and not more than 100 at. % and y being not less than 0 at. % and not more than 30 at. %) may be used as the second fixed magnetic layer 207. By using an amorphous alloy of $(Co_xFe_{100-x})_{100-y}B_y$ as the second fixed magnetic layer 207, the fluctuation of the characteristics of the sensing element 50A can be suppressed even in the case where the sizes of the sensing elements are small.

For example, it is favorable for the thickness of the second fixed magnetic layer 207 to be not less than 1.5 nm and not more than 5 nm. Thereby, for example, the strength of the unidirectional anisotropic magnetic field due to the pinning layer 206 can be stronger. For example, the strength of the antiferromagnetic coupling magnetic field between the second fixed magnetic layer 207 and the first fixed magnetic layer 209 via the magnetic coupling layer formed on the second fixed magnetic layer 207 can be stronger. For example, it is favorable for the magnetic thickness (the product (Bs·t) of a saturation magnetization Bs and a thickness t) of the second fixed magnetic layer 207 to be substantially equal to the magnetic thickness of the first fixed magnetic layer 209.

The saturation magnetization of the thin film of $Co_{40}Fe_{40}B_{20}$ is about 1.9 T (teslas). For example, in the case where a $Co_{40}Fe_{40}B_{20}$ layer having a thickness of 3 nm is used as the first fixed magnetic layer 209, the magnetic thickness of the first fixed magnetic layer 209 is 1.9 T×3 nm, i.e., 5.7 Tnm. On the other hand, the saturation magnetization of $Co_{75}Fe_{25}$ is about 2.1 T. The thickness of the second fixed magnetic layer 207 to obtain a magnetic thickness equal to that recited above is 5.7 Tnm/2.1 T, i.e., 2.7 nm. In such a case, it is favorable for a $Co_{75}Fe_{25}$ layer having a thickness of about 2.7 nm to be included in the second fixed magnetic layer 207. For example, a $Co_{75}Fe_{25}$ layer having a thickness of 2.5 nm is used as the second fixed magnetic layer 207.

In the sensing element 50A, a synthetic pinned structure of the second fixed magnetic layer 207, the magnetic coupling layer 208, and the first fixed magnetic layer 209 is used. A single pinned structure made of one fixed magnetic layer may be used instead. In the case where the single pinned structure is used, for example, a $Co_{40}Fe_{40}B_{20}$ layer having a thickness of 3 nm is used as the fixed magnetic layer. The same material as the second fixed magnetic layer 207 described above may be used as the ferromagnetic layer included in the fixed magnetic layer having the single pinned structure.

The magnetic coupling layer 208 causes antiferromagnetic coupling to occur between the second fixed magnetic layer 207 and the first fixed magnetic layer 209. The magnetic coupling layer 208 has a synthetic pinned structure. For example, Ru is used as the material of the magnetic coupling layer 208. For example, it is favorable for the thickness of the magnetic coupling layer 208 to be not less than 0.8 nm and not more than 1 nm. A material other than Ru may be used as the magnetic coupling layer 208 if the material causes sufficient antiferromagnetic coupling to occur between the second fixed magnetic layer 207 and the first fixed magnetic layer 209. For example, the thickness of the magnetic coupling layer 208 is set to be a thickness not less than 0.8 nm and not more than 1 nm corresponding to the second peak (2nd peak) of RKKY (Ruderman-Kittel-Kasuya-Yosida) coupling. Further, the thickness of the magnetic coupling layer 208 may be set to be a thickness not less than 0.3 nm and not more than 0.6 nm corresponding to the first peak (1st peak) of RKKY coupling. For example, Ru having a thickness of 0.9 nm is used as the material of the magnetic coupling layer 208. Thereby, highly reliable coupling is obtained more stably.

The magnetic layer that is included in the first fixed magnetic layer 209 contributes directly to the MR effect. For example, a Co—Fe—B alloy is used as the first fixed magnetic layer 209. Specifically, a $(Co_xFe_{100-x})_{100-y}B_y$ alloy (x being not less than 0 at. % and not more than 100 at. %, and y being not less than 0 at. % and not more than 30 at. %) may be used as the first fixed magnetic layer 209. For example, the fluctuation between the elements caused by crystal grains can be suppressed even in the case where the size of the sensing element 50A is small by using a $(Co_xFe_{100-x})_{100-y}B_y$ amorphous alloy as the first fixed magnetic layer 209.

The layer (e.g., a tunneling insulating layer (not shown)) that is formed on the first fixed magnetic layer 209 may be planarized. The defect density of the tunneling insulating layer can be reduced by planarizing the tunneling insulating layer. Thereby, a higher MR ratio is obtained with a lower resistance per area. For example, in the case where MgO is used as the material of the tunneling insulating layer, the (100) orientation of the MgO layer formed on the tunneling insulating layer can be strengthened by using a $(Co_xFe_{100-x})_{100-y}B_y$ amorphous alloy as the first fixed magnetic layer 209. A higher MR ratio is obtained by increasing the (100) orientation of the MgO layer. The $(Co_xFe_{100-x})_{100-y}B_y$ alloy crystallizes using the (100) plane of the MgO layer as a template when annealing. Therefore, good crystal conformation between the MgO and $(Co_xFe_{100-x})_{100-y}B_y$ alloy is obtained. A higher MR ratio is obtained by obtaining good crystal conformation.

Other than the Co—Fe—B alloy, for example, an Fe—Co alloy may be used as the first fixed magnetic layer 209.

A higher MR ratio is obtained as the thickness of the first fixed magnetic layer 209 increases. For example, a larger fixed magnetic field is obtained as the thickness of the first fixed magnetic layer 209 decreases. A trade-off relationship between the MR ratio and the fixed magnetic field exists for the thickness of the first fixed magnetic layer 209. In the case where the Co—Fe—B alloy is used as the first fixed magnetic layer 209, it is favorable for the thickness of the first fixed magnetic layer 209 to be not less than 1.5 nm and not more than 5 nm. It is more favorable for the thickness of the first fixed magnetic layer 209 to be not less than 2.0 nm and not more than 4 nm.

Other than the materials described above, the first fixed magnetic layer 209 may include a $Co_{90}Fe_{10}$ alloy having a fcc structure, Co having a hcp structure, or a Co alloy having a hcp structure. For example, at least one selected from the group consisting of Co, Fe, and Ni is used as the first fixed magnetic layer 209. An alloy that includes at least one material selected from these materials is used as the first fixed magnetic layer 209. For example, a higher MR ratio is obtained by using an FeCo alloy material having a bcc structure, a Co alloy having a cobalt composition of 50% or more, or a material (a Ni alloy) having a Ni composition of 50% or more as the first fixed magnetic layer 209.

For example, a Heusler magnetic alloy layer such as $Co_2MnGe$, $Co_2FeGe$, $Co_2MnSi$, $Co_2FeSi$, $Co_2MnAl$, $Co_2FeAl$, $Co_2MnGa_{0.5}Ge_{0.5}$, $Co_2FeGa_{0.5}Ge_{0.5}$, etc., also may be used as the first fixed magnetic layer 209. For example, a $Co_{40}Fe_{40}B_{20}$ layer having a thickness of 3 nm may be used as the first fixed magnetic layer 209.

For example, the intermediate layer 203 divides the magnetic coupling between the first fixed magnetic layer 209 and the free magnetic layer 210.

For example, the material of the intermediate layer 203 includes a metal, an insulator, or a semiconductor. For example, Cu, Au, Ag, or the like is used as the metal. In the case where a metal is used as the intermediate layer 203, the thickness of the intermediate layer is, for example, not less than about 1 nm and not more than about 7 nm. For example, magnesium oxide (MgO, etc.), aluminum oxide ($Al_2O_3$, etc.), titanium oxide (TiO, etc.), zinc oxide (ZnO, etc.), gallium oxide (Ga—O), or the like is used as the insulator or the semiconductor. In the case where the insulator or the semiconductor is used as the intermediate layer 203, the thickness of the intermediate layer 203 is, for example, not less than about 0.6 nm and not more than about 2.5 nm. For example, a CCP (Current-Confined-Path) spacer layer may be used as the intermediate layer 203. In the case where a CCP spacer layer is used as the spacer layer, for example, a structure is used in which a copper (Cu) metal path is formed inside an insulating layer of aluminum oxide ($Al_2O_3$). For example, a MgO layer having a thickness of 1.6 nm is used as the intermediate layer.

The free magnetic layer 210 includes a ferromagnet material. For example, the free magnetic layer 210 includes a ferromagnet material including Fe, Co, and Ni. For example, an FeCo alloy, a NiFe alloy, or the like is used as the material of the free magnetic layer 210. The free magnetic layer 210 may include a Co—Fe—B alloy, an Fe—Co—Si—B alloy, an Fe—Ga alloy having a large λs (magnetostriction constant), an Fe—Co—Ga alloy, a Tb-M-Fe alloy, a Tb-M1-Fe-M2 alloy, an Fe-M3-M4-B alloy, Ni, Fe—Al, ferrite, etc. For example, λs (the magnetostriction constant) is large for these materials. In the Tb-M-Fe alloy recited above, M is at least one selected from the group consisting of Sm, Eu, Gd, Dy, Ho, and Er. In the Tb-M1-Fe-M2 alloy recited above, M1 is at least one selected from the group consisting of Sm, Eu, Gd, Dy, Ho, and Er. M2 is at least one selected from the group consisting of Ti, Cr, Mn, Co, Cu, Nb, Mo, W, and Ta. In the Fe-M3-M4-B alloy recited above, M3 is at least one selected from the group consisting of Ti, Cr, Mn, Co, Cu, Nb, Mo, W, and Ta. M4 is at least one selected from the group consisting of Ce, Pr, Nd, Sm, Tb, Dy, and Er. $Fe_3O_4$, $(FeCo)_3O_4$, etc., are examples of the ferrite recited above. The thickness of the free magnetic layer 210 is, for example, 2 nm or more.

The free magnetic layer 210 may include a magnetic material including boron. The free magnetic layer 210 may include, for example, an alloy including boron (B) and at least one element selected from the group consisting of Fe, Co, and Ni. For example, the free magnetic layer 210 includes a Co—Fe—B alloy or an Fe—B alloy. For example, a $Co_{40}Fe_{40}B_{20}$ alloy is used. Ga, Al, Si, W, etc., may be added in the case where the free magnetic layer 210 includes an alloy including boron (B) and at least one element selected from the group consisting of Fe, Co, and Ni. For example, high magnetostriction is promoted by adding these elements. For example, an Fe—Ga—B alloy, an Fe—Co—Ga—B alloy, or an Fe—Co—Si—B alloy may be used as the free magnetic layer 210. By using such a magnetic material containing boron, the coercivity (Hc) of the free magnetic layer 210 is low; and the change of the magnetization direction for the strain is easy. Thereby, high sensitivity is obtained.

It is favorable for the boron concentration (e.g., the composition ratio of boron) of the free magnetic layer 210 to be 5 at. % (atomic percent) or more. Thereby, an amorphous structure is obtained easily. It is favorable for the boron concentration of the free magnetic layer to be 35 at. % or less. For example, the magnetostriction constant decreases when the boron concentration is too high. For example, it is favorable for the boron concentration of the free magnetic layer to be not less than 5 at. % and not more than 35 at. %; and it is more favorable to be not less than 10 at. % and not more than 30 at. %.

In the case where a portion of the magnetic layer of the free magnetic layer 210 includes $Fe_{1-y}B_y$ (0<y≤0.3) or $(Fe_zX_{1-z})_{1-y}B_y$ (X being Co or Ni, 0.8≤z<1, and 0<y≤0.3), it becomes easy to realize both a large magnetostriction constant λ and a low coercivity. Therefore, this is particularly favorable from the perspective of obtaining a high gauge factor. For example, $Fe_{80}B_{20}$ (4 nm) is used as the free magnetic layer 210. $Co_{40}Fe_{40}B_{20}$ (0.5 nm)/$Fe_{80}B_{20}$ (4 nm) may be used as the free magnetic layer 210.

The free magnetic layer 210 may have a multilayered structure. In the case where a tunneling insulating layer of MgO is used as the intermediate layer 203, it is favorable to provide a layer of a Co—Fe—B alloy at the portion of the free magnetic layer 210 contacting the intermediate layer 203. Thereby, a high magnetoresistance effect is obtained. In such a case, a layer of a Co—Fe—B alloy is provided on the intermediate layer 203; and another magnetic material that has a large magnetostriction constant is provided on the layer of the Co—Fe—B alloy. In the case where the free magnetic layer 210 has the multilayered structure, for example, the free magnetic layer 210 may include Co—Fe—B (2 nm)/Fe—Co—Si—B (4 nm), etc.

The capping layer 211 protects the layers provided under the capping layer 211. The capping layer 211 includes, for example, multiple metal layers. The capping layer 211 includes, for example, a two-layer structure (Ta/Ru) of a Ta layer and a Ru layer. The thickness of the Ta layer is, for example, 1 nm; and the thickness of the Ru layer is, for example, 5 nm. As the capping layer 211, another metal layer may be provided instead of the Ta layer and/or the Ru layer. The configuration of the capping layer 211 is arbitrary. For example, a nonmagnetic material is used as the capping layer 211. Another material may be used as the capping layer 211 as long as the material can protect the layers provided under the capping layer 211.

In the case where the free magnetic layer 210 includes a magnetic material containing boron, a diffusion suppression layer (not shown) of an oxide material and/or a nitride material may be provided between the free magnetic layer 210 and the capping layer 211. Thereby, for example, the diffusion of boron is suppressed. By using the diffusion suppression layer including an oxide layer or a nitride layer, the diffusion of the boron included in the free magnetic layer 210 can be suppressed; and the amorphous structure of the free magnetic layer 210 can be maintained. As the oxide material and/or the nitride material included in the diffusion suppression layer, for example, an oxide material or a nitride material including an element such as Mg, Al, Si, Ti, V, Cr, Mn, Fe, Co, Ni, Cu, Zn, Zr, Nb, Mo, Ru, Rh, Pd, Ag, Hf, Ta, W, Sn, Cd, Ga, or the like is used. The diffusion suppression layer is a layer that does not contribute to the magnetoresistance effect. It is favorable for the resistance per area of the diffusion suppression layer to be low. For example, it is favorable for the resistance per area of the diffusion suppression layer to be set to be lower than the resistance per area of the intermediate layer that contributes to the magnetoresistance effect. From the perspective of reducing the resistance per area of the diffusion suppression layer, it is favorable for the diffusion suppression layer to be an oxide or a nitride of Mg, Ti, V, Zn, Sn, Cd, or Ga. The barrier height of these materials is low. It is favorable to use an oxide having a strong chemical bond to suppress the diffusion of the boron. For example, a MgO layer of 1.5 nm is used. Oxynitrides are included in one of the oxide or the nitride.

In the case where the diffusion suppression layer includes an oxide or a nitride, it is favorable for the thickness of the diffusion suppression layer to be, for example, 0.5 nm or more. Thereby, the diffusion suppression function of the boron is realized sufficiently. It is favorable for the thickness of the diffusion suppression layer to be 5 nm or less. Thereby, for example, a low resistance per area is obtained. It is favorable for the thickness of the diffusion suppression layer to be not less than 0.5 nm and not more than 5 nm; and it is more favorable to be not less than 1 nm and not more than 3 nm.

At least one selected from the group consisting of magnesium (Mg), silicon (Si), and aluminum (Al) may be used as the diffusion suppression layer. A material that includes these light elements may be used as the diffusion suppression layer. These light elements produce compounds by bonding with boron. For example, at least one of a Mg—B compound, an Al—B compound, or a Si—B compound is formed at the portion including the interface between the diffusion suppression layer and the free magnetic layer 210. These compounds suppress the diffusion of boron.

Another metal layer, etc., may be inserted between the diffusion suppression layer and the free magnetic layer 210. In the case where the distance between the diffusion suppression layer and the free magnetic layer 210 is too long, boron diffuses between the diffusion suppression layer and the free magnetic layer 210; and the boron concentration in the free magnetic layer 210 undesirably decreases. Therefore, it is favorable for the distance between the diffusion suppression layer and the free magnetic layer 210 to be 10 nm or less; and it is more favorable to be 3 nm or less.

FIG. 9 is a schematic perspective view illustrating a portion of another pressure sensor according to the embodiment.

As shown in FIG. 9, other than an insulating layer 213 being provided, the sensing element 50AA is similar to the sensing element 50A. The insulating layer 213 is provided between the lower electrode 204 and the upper electrode 212. The insulating layer 213 is arranged with the free magnetic layer 210 and the first fixed magnetic layer 209 in a direction intersecting the direction connecting the lower electrode 204 and the upper electrode 212. The portions other than the insulating layer 213 are similar to those of the sensing element 50A; and a description is therefore omitted.

The insulating layer 213 includes, for example, aluminum oxide (e.g., $Al_2O_3$), silicon oxide (e.g., $SiO_2$), etc. The leakage current of the sensing element 50AA is suppressed by the insulating layer 213. The insulating layer 213 may be provided in the sensing elements described below.

FIG. 10 is a schematic perspective view illustrating a portion of another pressure sensor according to the embodiment.

As shown in FIG. 10, a hard bias layer 214 is further provided in the sensing element 50AB. Otherwise, the sensing element 50AB is similar to the sensing element 50A. The hard bias layer 214 is provided between the lower electrode 204 and the upper electrode 212. The free magnetic layer 210 and the first fixed magnetic layer 209 are disposed between two portions of the hard bias layer 214 in a direction intersecting the direction connecting the lower electrode 204 and the upper electrode 212. Otherwise, the sensing element 50AB is similar to the sensing element 50AA.

The hard bias layer 214 sets the magnetization direction of the free magnetic layer 210 by the magnetization of the hard bias layer 214. The magnetization direction of the free magnetic layer 210 is set to the desired direction by the hard bias layer 214 in a state in which pressure from the outside is not applied to the film portion 70d.

The hard bias layer 214 includes, for example, Co—Pt, Fe—Pt, Co—Pd, Fe—Pd, etc. For example, the magnetic anisotropy and the coercivity are relatively high for these materials. These materials are, for example, hard magnetic materials. The hard bias layer 214 may include, for example, an alloy in which an added element is further added to Co—Pt, Fe—Pt, Co—Pd, or Fe—Pd. The hard bias layer 214 may include, for example, CoPt (the proportion of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), FePt (the proportion of Pt being not less than 40 at. % and not more than 60 at. %), etc. In the case where such a material is used, by applying an external magnetic field that is larger than the coercivity of the hard bias layer 214, the direction of the magnetization of the hard bias layer 214 is set (fixed) in the direction in which the external magnetic field is applied. The thickness of the hard bias layer 214 (e.g., the length along the direction from the lower electrode 204 toward the upper electrode) is, for example, not less than 5 nm and not more than 50 nm.

In the case where the insulating layer 213 is disposed between the lower electrode 204 and the upper electrode 212, $SiO_x$ or $AlO_x$ is used as the material of the insulating layer 213. A not-shown foundation layer may be provided between the insulating layer 213 and the hard bias layer 214. Cr, Fe—Co, or the like is used as the material of the foundation layer for the hard bias layer 214 in the case where the hard bias layer 214 includes a hard magnetic material such as Co—Pt, Fe—Pt, Co—Pd, Fe—Pd, etc.

The hard bias layer 214 may have a structure of being stacked with a not-shown pinning layer for a hard bias layer. In such a case, the direction of the magnetization of the hard bias layer 214 can be set (fixed) by the exchange coupling of the hard bias layer 214 and the pinning layer for the hard bias layer. In such a case, the hard bias layer 214 includes a ferromagnetic material of at least one of Fe, Co, or Ni, or an alloy including at least one type of these elements. In such a case, the hard bias layer 214 includes, for example, a $Co_xFe_{100-x}$ alloy (x being not less than 0 at. % and not more than 100 at. %), a $Ni_xFe_{100-x}$ alloy (x being not less than 0 at. % and not more than 100 at. %), or a material in which a nonmagnetic element is added to these alloys. A material similar to the first fixed magnetic layer 209 recited above is used as the hard bias layer 214. The pinning layer for the hard bias layer includes a material similar to the pinning layer 206 inside the sensing element 50A recited above. In the case where the pinning layer for the hard bias layer is provided, a foundation layer similar to the material included in the foundation layer 205 may be provided under the pinning layer for the hard bias layer. The pinning layer for the hard bias layer may be provided at a lower portion or at an upper portion of the hard bias layer. In such a case, the magnetization direction of the hard bias layer 214 is determined by heat treatment in a magnetic field similarly to the pinning layer 206.

The hard bias layer 214 and the insulating layer 213 recited above are applicable to any sensing element according to the embodiments. By using the stacked structure of the hard bias layer 214 and the pinning layer for the hard bias layer, the orientation of the magnetization of the hard bias layer 214 can be maintained easily even when a large external magnetic field is applied to the hard bias layer 214 in a short period of time.

Figure 11:
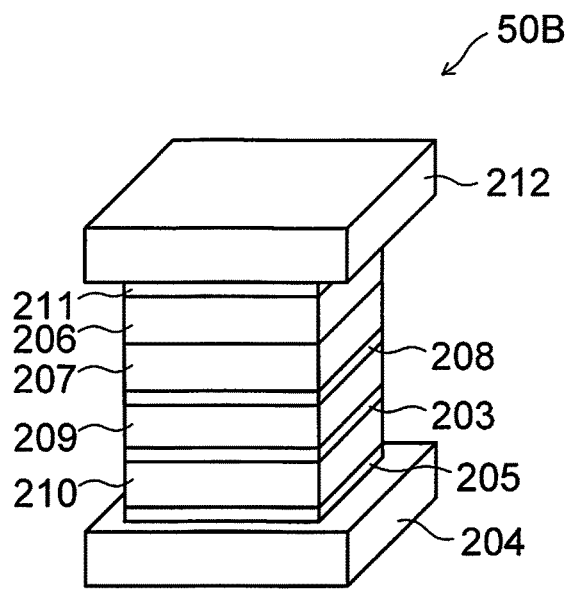
FIG. 11 is a schematic perspective view illustrating a portion of another pressure sensor according to the embodiment.

FIG. 11 is a schematic perspective view illustrating a portion of another pressure sensor according to the embodiment.

In the sensing element 50B as shown in FIG. 11, the lower electrode 204, the foundation layer 205, the free magnetic layer 210, the intermediate layer 203, the first fixed magnetic layer 209, the magnetic coupling layer 208, the second fixed magnetic layer 207, the pinning layer 206, the capping layer 211, and the upper electrode 212 are stacked in order. For example, the first fixed magnetic layer 209 corresponds to one of the first opposing magnetic layer 11b or the second opposing magnetic layer 12b. For example, the free magnetic layer 210 corresponds to one of the first magnetic layer 11a or the second magnetic layer 12a. The intermediate layer 203 corresponds to one of the first intermediate layer 11c or the second intermediate layer 12c. The sensing element 50B is, for example, a top spin-valve type.

The foundation layer 205 includes, for example, a stacked film of tantalum and copper (Ta/Cu). The thickness (the length in the Z-axis direction) of the Ta layer is, for example, 3 nm. The thickness of the Cu layer is, for example, 5 nm. The free magnetic layer 210 includes, for example, $Co_{40}Fe_{40}B_{20}$ having a thickness of 4 nm. The intermediate layer 203 includes, for example, a MgO layer having a thickness of 1.6 nm. The first fixed magnetic layer 209 includes, for example, $Co_{40}Fe_{40}B_{20}/Fe_{50}Co_{50}$. The thickness of the $Co_{40}Fe_{40}B_{20}$ layer is, for example, 2 nm. The thickness of the $Fe_{50}Co_{50}$ layer is, for example, 1 nm. The magnetic coupling layer 208 includes, for example, a Ru layer having a thickness of 0.9 nm. The second fixed magnetic layer 207 includes, for example, a $Co_{75}Fe_{25}$ layer having a thickness of 2.5 nm. The pinning layer 206 includes, for example, an IrMn layer having a thickness of 7 nm. The capping layer 211 includes, for example, Ta/Ru. The thickness of the Ta layer is, for example, 1 nm. The thickness of the Ru layer is, for example, 5 nm.

The materials of the layers included in the sensing element 50B may be the vertically inverted materials of the layers included in the sensing element 50A. The diffusion suppression layer recited above may be provided between the foundation layer 205 and the free magnetic layer 210 of the sensing element 50B.

Figure 12:
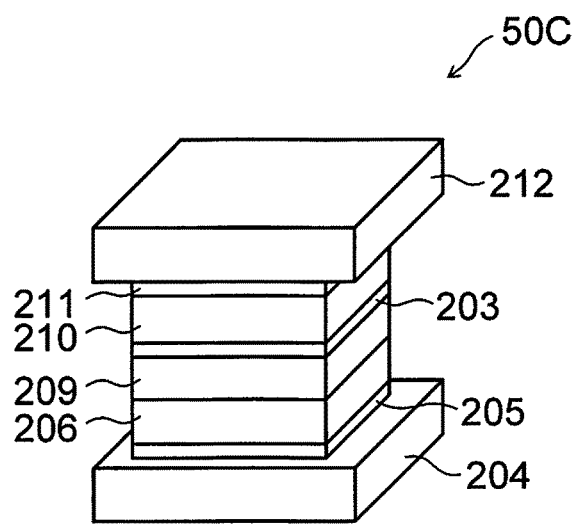
FIG. 12 is a schematic perspective view illustrating a portion of another pressure sensor according to the embodiment.

FIG. 12 is a schematic perspective view illustrating a portion of another pressure sensor according to the embodiment.

In the sensing element 50C as shown in FIG. 12, the lower electrode 204, the foundation layer 205, the pinning layer 206, the first fixed magnetic layer 209, the intermediate layer 203, the free magnetic layer 210, and the capping layer 211 are stacked in this order. For example, the first fixed magnetic layer 209 corresponds to one of the first opposing magnetic layer 11b or the second opposing magnetic layer 12b. For example, the free magnetic layer 210 corresponds to one of the first magnetic layer 11a or the second magnetic layer 12a. The intermediate layer 203 corresponds to one of the first intermediate layer 11c or the second intermediate layer 12c. For example, the sensing element 50C has a single pinned structure that uses a single fixed magnetic layer.

The foundation layer 205 includes, for example, Ta/Ru. The thickness (the length in the Z-axis direction) of the Ta layer is, for example, 3 nm. The thickness of the Ru layer is, for example, 2 nm. The pinning layer 206 includes, for example, an IrMn layer having a thickness of 7 nm. The first fixed magnetic layer 209 includes, for example, a $Co_{40}Fe_{40}B_{20}$ layer having a thickness of 3 nm. The intermediate layer 203 includes, for example, a MgO layer having a thickness of 1.6 nm. The free magnetic layer 210 includes, for example, $Co_{40}Fe_{40}B_{20}$ having a thickness of 4 nm. The capping layer 211 includes, for example, Ta/Ru. The thickness of the Ta layer is, for example, 1 nm. The thickness of the Ru layer is, for example, 5 nm.

For example, materials similar to the materials of the layers of the sensing element 50A are used as the materials of the layers of the sensing element 50C.

Figure 13:
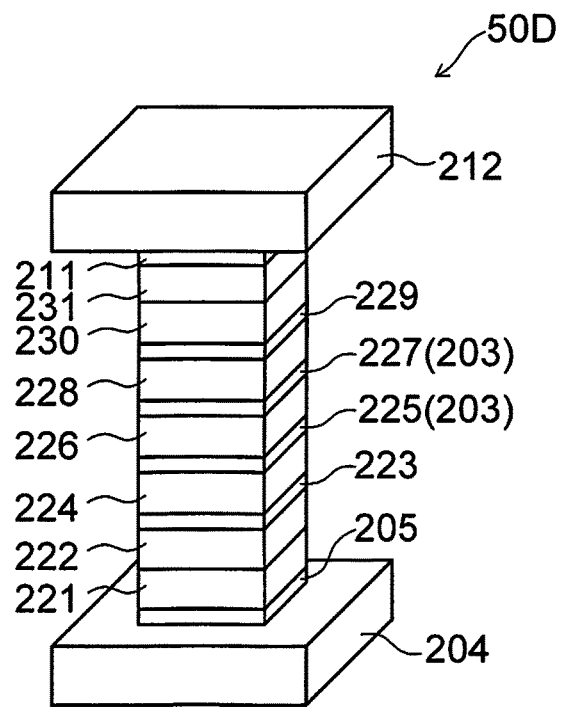
FIG. 13 is a schematic perspective view illustrating a portion of another pressure sensor according to the embodiment.

FIG. 13 is a schematic perspective view illustrating a portion of another pressure sensor according to the embodiment.

In the sensing element 50D as shown in FIG. 13, the lower electrode 204, the foundation layer 205, a lower pinning layer 221, a lower second fixed magnetic layer 222, a lower magnetic coupling layer 223, a lower first fixed magnetic layer 224, a lower intermediate layer 225, a free magnetic layer 226, an upper intermediate layer 227, an upper first fixed magnetic layer 228, an upper magnetic coupling layer 229, an upper second fixed magnetic layer 230, an upper pinning layer 231, and the capping layer 211 are stacked in order. For example, the lower first fixed magnetic layer 224 and the upper first fixed magnetic layer 228 correspond to one of the first opposing magnetic layer 11b or the second opposing magnetic layer 12b. For example, the free magnetic layer 226 corresponds to one of the first magnetic layer 11a or the second magnetic layer 12a.

The foundation layer 205 includes, for example, Ta/Ru. The thickness (the length in the Z-axis direction) of the Ta layer is, for example, 3 nanometers (nm). The thickness of the Ru layer is, for example, 2 nm. The lower pinning layer 221 includes, for example, an IrMn layer having a thickness of 7 nm. The lower second fixed magnetic layer 222 includes, for example, a $Co_{75}Fe_{25}$ layer having a thickness of 2.5 nm. The lower magnetic coupling layer 223 includes, for example, a Ru layer having a thickness of 0.9 nm. The lower first fixed magnetic layer 224 includes, for example, a $Co_{40}Fe_{40}B_{20}$ layer having a thickness of 3 nm. The lower intermediate layer 225 includes, for example, a MgO layer having a thickness of 1.6 nm. The free magnetic layer 226 includes, for example, $Co_{40}Fe_{40}B_{20}$ having a thickness of 4 nm. The upper intermediate layer 227 includes, for example, a MgO layer having a thickness of 1.6 nm. The upper first fixed magnetic layer 228 includes, for example, $Co_{40}Fe_{40}B_{20}/Fe_{50}Co_{50}$. The thickness of the $Co_{40}Fe_{40}B_{20}$ layer is, for example, 2 nm. The thickness of the $Fe_{50}Co_{50}$ layer is, for example, 1 nm. The upper magnetic coupling layer 229 includes, for example, a Ru layer having a thickness of 0.9 nm. The upper second fixed magnetic layer 230 includes, for example, a $Co_{75}Fe_{25}$ layer having a thickness of 2.5 nm. The upper pinning layer 231 includes, for example, an IrMn layer having a thickness of 7 nm. The capping layer 211 includes, for example, Ta/Ru. The thickness of the Ta layer is, for example, 1 nm. The thickness of the Ru layer is, for example, 5 nm.

For example, materials similar to the materials of the layers of the sensing element 50A are used as the materials of the layers of the sensing element 50D.

Figure 14:
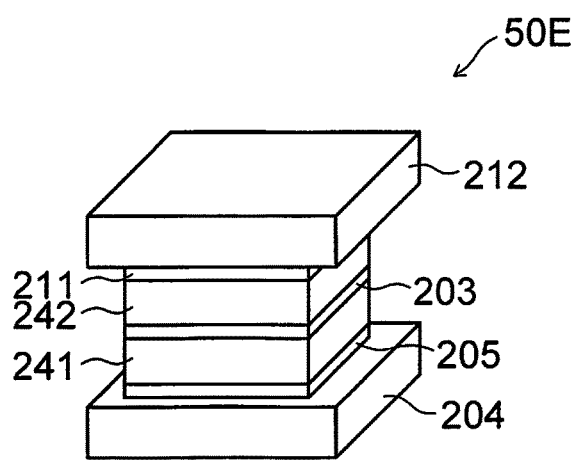
FIG. 14 is a schematic perspective view illustrating a portion of another pressure sensor according to the embodiment.

FIG. 14 is a schematic perspective view illustrating a portion of another pressure sensor according to the embodiment.

In the sensing element 50E as shown in FIG. 14, the lower electrode 204, the foundation layer 205, a first free magnetic layer 241, the intermediate layer 203, a second free magnetic layer 242, the capping layer 211, and the upper electrode 212 are stacked in this order. The first free magnetic layer 241 corresponds to one of the first magnetic layer 11a or the second magnetic layer 12a. The second free magnetic layer 242 corresponds to one of the first opposing magnetic layer 11b or the second opposing magnetic layer 12b. In the example, the magnetizations of the first opposing magnetic layer 11b and the second opposing magnetic layer 12b are changeable.

The foundation layer 205 includes, for example, Ta/Cu. The thickness (the length in the Z-axis direction) of the Ta layer is, for example, 3 nm. The thickness of the Cu layer is, for example, 5 nm. The first free magnetic layer 241 includes, for example, $Co_{40}Fe_{40}B_{20}$ having a thickness of 4 nm. In the second example, the intermediate layer 203 includes, for example, $Co_{40}Fe_{40}B_{20}$ having a thickness of 4 nm. The capping layer 211 includes, for example, Cu/Ta/Ru. The thickness of the Cu layer is, for example, 5 nm. The thickness of the Ta layer is, for example, 1 nm. The thickness of the Ru layer is, for example, 5 nm.

Materials similar to the materials of the layers of the sensing element 50A are used as the materials of the layers of the sensing element 50E. For example, materials similar to those of the free magnetic layer 210 of the sensing element 50A may be used as the materials of the first free magnetic layer 241 and the second free magnetic layer 242.

Third Embodiment

FIG. 15 is a schematic view illustrating a microphone according to a third embodiment.

As shown in FIG. 15, the microphone 610 according to the embodiment includes any pressure sensor according to the embodiments or a pressure sensor according to a modification of the embodiments recited above. In the example, the pressure sensor 110 is used as the pressure sensor.

For example, the microphone 610 is provided in a personal digital assistant 710. For example, the film portion 70d of the pressure sensor 110 is substantially parallel to the surface in which a display unit 620 of the personal digital assistant 710 is provided. The disposition of the film portion 70d is arbitrary. According to the embodiment, a microphone in which the dynamic range can be enlarged can be provided. For example, the microphone 610 according to the embodiment may be provided in an IC recorder, a pin microphone, etc.

FIG. 16 is a schematic cross-sectional view illustrating another microphone according to the third embodiment.

A microphone 320 (an acoustic microphone) according to the embodiment includes a printed circuit board 321, a cover 323, and a pressure sensor. Any pressure sensor according to the embodiments or a modification of the embodiments is used as the pressure sensor. In the example, the pressure sensor 110 is used as the pressure sensor. The printed circuit board 321 includes, for example, a circuit such as an amplifier, etc. An acoustic hole 325 is provided in the cover 323. Sound 329 passes through the acoustic hole 325 and enters the interior of the cover 323. The microphone 320 responds to the sound pressure. A highly-sensitive microphone 320 is obtained by using the highly-sensitive pressure sensor 110. For example, the pressure sensor 110 is mounted on the printed circuit board 321; and electrical signal lines are provided. The cover 323 is provided on the printed circuit board 321 to cover the pressure sensor 110. A microphone in which the dynamic range can be enlarged can be provided.

Fourth Embodiment

FIG. 17A and FIG. 17B are schematic views illustrating a blood pressure sensor according to a fourth embodiment.

FIG. 17A is a schematic plan view illustrating skin on an arterial vessel of a human. FIG. 17B is a line H1-H2 cross-sectional view of FIG. 17A.

The blood pressure sensor 330 according to the embodiment includes any pressure sensor according to the embodiments or a modification of the embodiments. In the example, the pressure sensor 110 is used as the pressure sensor. The pressure sensor 110 is pressed onto the skin 333 on the arterial vessel 331. Thereby, the blood pressure sensor 330 can continuously perform blood pressure measurements. According to the embodiment, a blood pressure sensor in which the dynamic range can be enlarged can be provided. The blood pressure can be measured with high sensitivity.

Fifth Embodiment

Figure 18:
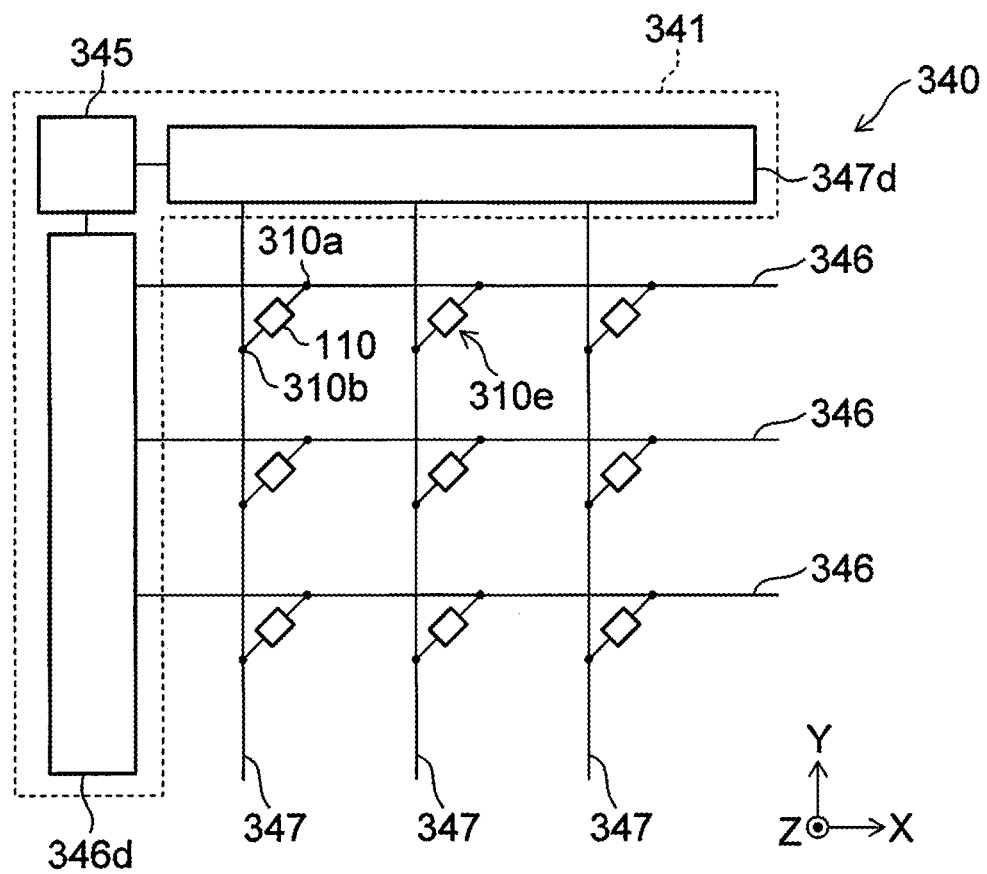
FIG. 18 is a schematic view illustrating a touch panel according to a fifth embodiment.

FIG. 18 is a schematic view illustrating a touch panel according to a fifth embodiment.

The touch panel 340 according to the embodiment includes any pressure sensor according to the embodiments or a modification of the embodiments. In the example, the pressure sensor 110 is used as the pressure sensor. In the touch panel 340, the pressure sensors 110 are mounted to at least one of the interior of the display or the exterior of the display.

For example, the touch panel 340 includes multiple first interconnects 346, multiple second interconnects 347, the multiple pressure sensors 110, and a controller 341.

In the example, the multiple first interconnects 346 are arranged along the Y-axis direction. Each of the multiple first interconnects 346 extends along the X-axis direction. The multiple second interconnects 347 are arranged along the X-axis direction. Each of the multiple second interconnects 347 extends along the Y-axis direction.

The multiple pressure sensors 110 are provided respectively at the intersections between the multiple first interconnects 346 and the multiple second interconnects 347. One pressure sensor 110 is used as one sensing component 310e for sensing. Here, the intersection includes the position where the first interconnect 346 and the second interconnect 347 intersect and includes the region at the periphery of the position.

One end 310a of each of the multiple pressure sensors 110 is connected respectively to the multiple first interconnects 346. One other end 310b of each of the multiple pressure sensors 110 is connected respectively to the multiple second interconnects 347.

The controller 341 is connected to the multiple first interconnects 346 and the multiple second interconnects 347. For example, the controller 341 includes a first interconnect circuit 346d that is connected to the multiple first interconnects 346, a second interconnect circuit 347d that is connected to the multiple second interconnects 347, and a control circuit 345 that is connected to the first interconnect circuit 346d and the second interconnect circuit 347d. The pressure sensor 110 is compact and can perform highly-sensitive pressure sensing. Therefore, it is possible to realize a high definition touch panel.

According to the embodiment, a touch panel in which the dynamic range can be enlarged can be provided. A highly-sensitive touch input is possible.

Other than the applications recited above, the pressure sensors according to the embodiments are applicable to an atmospheric pressure sensor, an air pressure sensor of a tire, etc. The pressure sensors according to the embodiments are applicable to various pressure sensing.

According to the embodiments, a pressure sensor, a microphone, a blood pressure sensor, and a touch panel in which the dynamic range can be enlarged can be provided.

Figure 19:
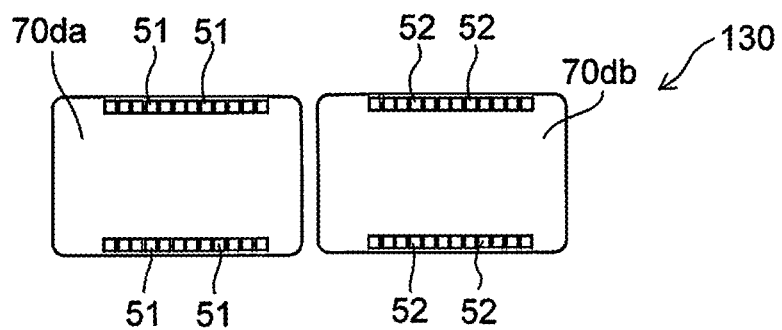
FIG. 19 is a schematic plan view illustrating a pressure sensor.

FIG. 19 is a schematic plan view illustrating a pressure sensor.

As shown in FIG. 19, the pressure sensor 130 includes a first film portion 70da that is deformable, the first sensing element 51 that is fixed to the first film portion 70da, a second film portion 70db that is deformable, and the second sensing element 52 that is fixed to the second film portion 70db. For example, the second material of the second sensing element 52 is different from the first material of the first sensing element 51. For example, the third magnetic layer 43 and the fourth magnetic layer 44 may be provided. In such a case, the configurations described in reference to FIG. 6A to FIG. 6D or FIG. 7A and FIG. 7B are applied to the third magnetic layer 43 and the fourth magnetic layer 44.

Sixth Embodiment

Figure 20:
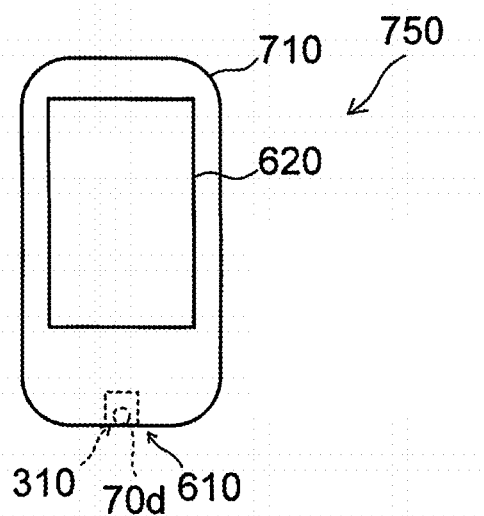
FIG. 20 is a schematic view illustrating an electronic device according to a sixth embodiment.

FIG. 20 is a schematic view illustrating the electronic device according to the sixth embodiment.

As shown in FIG. 20, the electronic device 750 according to the embodiment is, for example, the information terminal 710. For example, the microphone 610 is provided in the information terminal 710.

The microphone 610 includes, for example, the pressure sensor 310. For example, a film portion 70d is substantially parallel to the surface of the information terminal 710 where a display unit 620 is provided. The disposition of the film portion 70d is arbitrary.

Figure 21A:
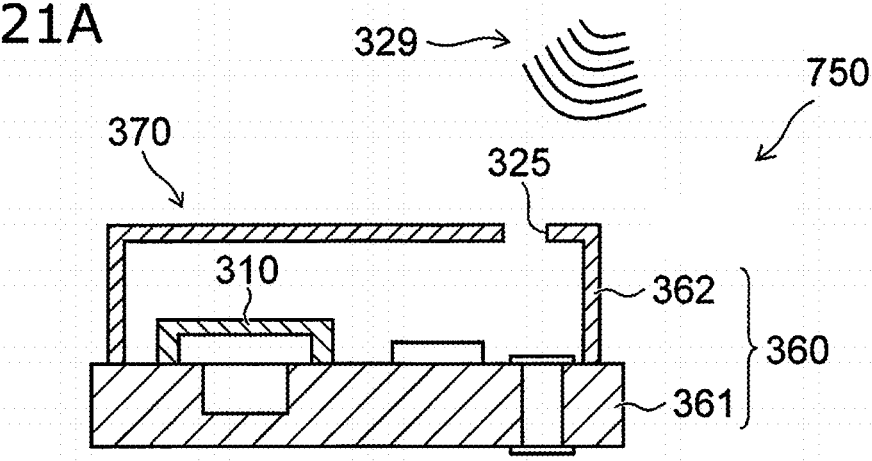
FIG. 21A and FIG. 21B are schematic cross-sectional views illustrating the electronic device according to the sixth embodiment.
Figure 21B:
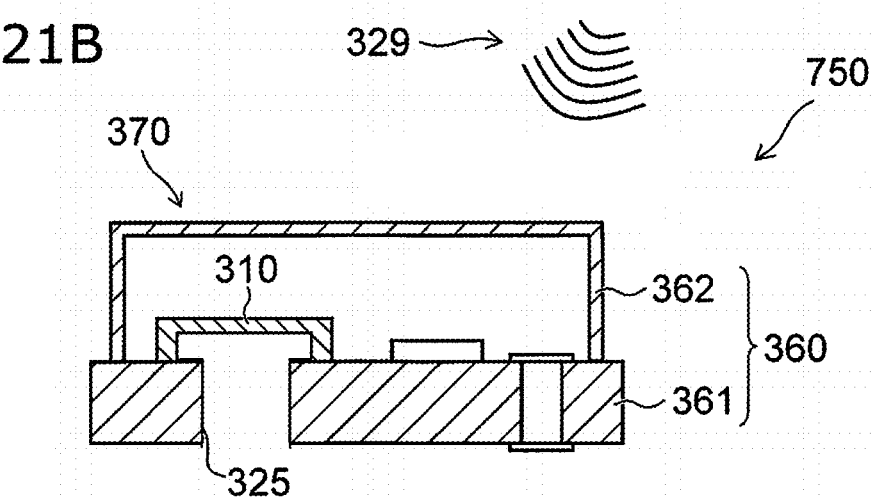

FIG. 21A and FIG. 21B are schematic cross-sectional views illustrating the electronic device according to the sixth embodiment.

As shown in FIG. 21A and FIG. 21B, the electronic device 750 (e.g., the microphone 370 (the acoustic microphone)) includes a housing 360, a cover 362, and the pressure sensor 310. The housing 360 includes, for example, a substrate 361 (e.g., a printed circuit board) and a cover 362. The substrate 361 includes, for example, a circuit such as an amplifier, etc. An acoustic hole 325 is provided in the housing 360 (at least one of the substrate 361 or the cover 362). Sound 329 passes through the acoustic hole 325 and enters the interior of the cover 362. The microphone 370 is sensitive to the sound pressure. For example, the pressure sensor 310 is mounted on the substrate 361; and electrical signal lines are provided. The cover 362 is provided on the substrate 361 to cover the pressure sensor 310. Thus, the housing 360 is provided around the sensor 310. For example, the first sensor unit 51a and the film portion 71 are disposed between the substrate 361 and the cover 362. For example, the sensor 310 is disposed between the substrate 361 and the cover 362.

Embodiments can include following configurations:

(Configuration 1) A sensor, comprising:
a film portion, the film portion being deformable;
a first sensing element fixed to the film portion, the first sensing element including a first magnetic layer of a first material, a first opposing magnetic layer, and a first intermediate layer, the first intermediate layer being provided between the first magnetic layer and the first opposing magnetic layer; and
a second sensing element fixed to the film portion, the second sensing element including a second magnetic layer of a second material, a second opposing magnetic layer, and a second intermediate layer, the second material being different from the first material, the second intermediate layer being provided between the second magnetic layer and the second opposing magnetic layer.

(Configuration 2) The sensor according to configuration 1, wherein
the first magnetic layer includes at least one of Fe, Co, or Ni with a first concentration, and
the second magnetic layer includes the at least one of Fe, Co, or Ni with a second concentration different from the first concentration.

(Configuration 3) The sensor according to configuration 1, wherein
the first magnetic layer includes Fe,
the second magnetic layer includes Fe, and
a concentration of Fe in the second magnetic layer is different from a concentration of Fe in the first magnetic layer.

(Configuration 4) The sensor according to configuration 1, wherein
the first magnetic layer includes at least one of Fe, Co, or Ni, and B,
the second magnetic layer includes at least one of Fe, Co, or Ni, and B, and
a concentration of B in the second magnetic layer is lower than a concentration of B in the first magnetic layer.

(Configuration 5) The sensor according to one of configurations 3 or 4, wherein
the first magnetic layer includes an amorphous region, and
the second magnetic layer includes a crystal region.

(Configuration 6) The sensor according to one of configurations 1-5, wherein
a composition ratio of Fe of the first magnetic layer is not less than 60 at. % and not more than 100 at. %, and
a composition ratio of Fe of the second magnetic layer is not less than 0 at. % but less than 60 at. %.

(Configuration 7) The sensor according to one of configurations 1-5, wherein
a composition ratio of B of the first magnetic layer is not less than 10 at. % and not more than 30 at. %, and
a composition ratio of B of the second magnetic layer is not less than 0 at. % but less than 10 at. %.

(Configuration 8) A sensor, comprising:
a film portion, the film portion being deformable;
a first sensing element fixed to the film portion, the first sensing element including a first magnetic layer, a first opposing magnetic layer, and a first intermediate layer, the first intermediate layer being provided between the first magnetic layer and the first opposing magnetic layer;
a second sensing element fixed to the film portion, the second sensing element including a second magnetic layer, a second opposing magnetic layer, and a second intermediate layer, the second intermediate layer being provided between the second magnetic layer and the second opposing magnetic layer;
a third magnetic layer; and
a fourth magnetic layer,
the third magnetic layer having
a first length along a first direction, the first direction being from the film portion toward the first sensing element,
a second length along a second direction perpendicular to the first direction,
a third length along a third direction perpendicular to the first direction and perpendicular to the second direction,
a first composition, and
a third magnetization direction,
the fourth magnetic layer having at least one of
a fourth length along the first direction, the fourth length being different from the first length,
a fifth length along the second direction, the fifth length being different from the second length,
a sixth length along the third direction, the sixth length being different from the third length,
a second composition different from the first composition, or
a fourth magnetization direction different from the third magnetization direction.

(Configuration 9) The sensor according to configuration 8, wherein
the first metal includes at least one selected from the group consisting of a first alloy, a second alloy, a third alloy, and a fourth alloy, the first alloy includes Co and Pt, the second alloy includes Fe and Pt, the third alloy includes Co and Pd, the fourth alloy includes Fe and Pd; and
the second metal includes at least one selected from the group consisting of a sixth alloy, a seventh alloy, an eighth alloy, and a ninth alloy, the sixth alloy includes Co and Pt, the seventh alloy includes Fe and Pt, the eighth alloy includes Co and Pd, the ninth alloy includes Fe and Pd.

(Configuration 10) The sensor according to configuration 9, wherein
the first alloy includes $(Co_xPt_{100-x})_{100-y}Cr_y$,
the x is not less than 50 at. % and not more than 85 at. %, and
the y is not less than 0 at. % and not more than 40 at. %.

(Configuration 11) The sensor according to configuration 8, wherein the third magnetic layer includes a first film and a second film, the first film includes at least one of Fe, Co, or Ni, and the second film includes at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O; and the fourth magnetic layer includes a third film and a fourth film, the third film includes at least one of Fe, Co, or Ni, and the fourth film includes at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O.

(Configuration 12) The sensor according to configuration 11, wherein the second film overlaps the first film in the first direction, and the fourth film overlaps the third film in the first direction.

(Configuration 13) A sensor, comprising:

a film portion, the film portion being deformable;

a first sensing element fixed to the film portion, the first sensing element including a first magnetic layer, a first opposing magnetic layer, and a first intermediate layer, the first intermediate layer being provided between the first magnetic layer and the first opposing magnetic layer;

a second sensing element fixed to the film portion, the second sensing element including a second magnetic layer, a second opposing magnetic layer, and a second intermediate layer, the second intermediate layer being provided between the second magnetic layer and the second opposing magnetic layer;

a third magnetic layer including at least one selected from the group consisting of a first alloy, a second alloy, a third alloy, and a fourth alloy, the first alloy including Co and Pt, the second alloy including Fe and Pt, the third alloy including Co and Pd, the fourth alloy including Fe and Pd; and a fourth magnetic layer including at least one selected from the group consisting of a sixth alloy, a seventh alloy, an eighth alloy, and a ninth alloy, the sixth alloy including Co and Pt, the seventh alloy including Fe and Pt, the eighth alloy including Co and Pd, the ninth alloy including Fe and Pd, the third magnetic layer having a first distance between the first magnetic layer and the third magnetic layer, the fourth magnetic layer having a second distance between the second magnetic layer and the fourth magnetic layer, the second distance being different from the first distance, the first distance being shorter than a distance between the first magnetic layer and the fourth magnetic layer, the second distance being shorter than a distance between the second magnetic layer and the third magnetic layer.

(Configuration 14) A sensor, comprising:

a film portion, the film portion being deformable;

a first sensing element fixed to the film portion, the first sensing element including a first magnetic layer, a first opposing magnetic layer, and a first intermediate layer, the first intermediate layer being provided between the first magnetic layer and the first opposing magnetic layer;

a second sensing element fixed to the film portion, the second sensing element including a second magnetic layer, a second opposing magnetic layer, and a second intermediate layer, the second intermediate layer being provided between the second magnetic layer and the second opposing magnetic layer;

the third magnetic layer including a first film and a second film, the first film including at least one of Fe, Co, or Ni, and the second film including at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O; and the fourth magnetic layer including a third film and a fourth film, the third film including at least one of Fe, Co, or Ni, and the fourth film including at least one selected from the group consisting of Ir—Mn, Pt—Mn, Pd—Pt—Mn, Ru—Mn, Rh—Mn, Ru—Rh—Mn, Fe—Mn, Ni—Mn, Cr—Mn—Pt, and Ni—O, the third magnetic layer having a first distance between the first magnetic layer and the third magnetic layer, the fourth magnetic layer having a second distance between the second magnetic layer and the fourth magnetic layer, the second distance being different from the first distance, the first distance being shorter than a distance between the first magnetic layer and the fourth magnetic layer, the second distance being shorter than a distance between the second magnetic layer and the third magnetic layer.

(Configuration 15) The sensor according to configuration 14, wherein the second film overlaps the first film in the first direction, and the fourth film overlaps the third film in the first direction.

(Configuration 16) The sensor according to one of configurations 1-15, wherein a first magnetization of the first magnetic layer changes according to a deformation of the film portion, and a second magnetization of the second magnetic layer changes according to the deformation of the film portion.

(Configuration 17) The sensor according to one of configurations 1-16, wherein a resistance between the first magnetic layer and the first opposing magnetic layer changes according to a deformation of the film portion.

(Configuration 18) The sensor according to one of configurations 1-17, wherein the first sensing element is most proximal to a first portion of an outer edge of the film portion, the second sensing element is most proximal to a second portion of the outer edge, and a difference between a first spacing and a second spacing is not more than 0.2 times the first spacing, the first spacing being between the first sensing element and the first portion, the second spacing being between the second sensing element and the second portion.

(Configuration 19) The sensor according to one of configurations 1-18, further comprising a processor connected to the first sensing element and the second sensing element, the processor implementing a first operation and a second operation, the first operation outputting a first output signal corresponding to a first signal obtained from the first sensing element, the second operation outputting a second output signal corresponding to a second signal obtained from the second sensing element.

(Configuration 20. A sensor, comprising:

a film portion, the film portion being deformable;

a first sensing element fixed to the film portion, the first sensing element including a first magnetic layer, a first opposing magnetic layer, and a first intermediate layer, the first intermediate layer being provided between the first magnetic layer and the first opposing magnetic layer;

a second sensing element fixed to the film portion, the second sensing element including a second magnetic layer, a second opposing magnetic layer, and a second intermediate layer, the second intermediate layer being provided between the second magnetic layer and the second opposing magnetic layer;

a processor connected to the first sensing element and the second sensing element, the processor implementing a first operation and a second operation, the first operation outputting a first output signal corresponding to a first signal obtained from the first sensing element, the second operation outputting a second output signal corresponding to a second signal obtained from the second sensing element.

(Configuration 21) The sensor according to configuration 20, wherein the processor implements the first operation when a first amplitude of the first signal is wider than a second amplitude of the second signal and implements the second operation when the second amplitude is wider than the first amplitude.

(Configuration 22) The sensor according to one configurations 1-21, further comprising:
 a substrate; and
 a cover,
 the film portion, first sensing element, and the second sensing element being provided between the substrate and the cover.

(Configuration 23) A microphone comprising:
 a sensor including:
 a film portion, the film portion being deformable;
 a first sensing element fixed to the film portion, the first sensing element including a first magnetic layer of a first material, a first opposing magnetic layer, and a first intermediate layer, the first intermediate layer being provided between the first magnetic layer and the first opposing magnetic layer; and
 a second sensing element fixed to the film portion, the second sensing element including a second magnetic layer of a second material, a second opposing magnetic layer, and a second intermediate layer, the second material being different from the first material, the second intermediate layer being provided between the second magnetic layer and the second opposing magnetic layer.

(Configuration 24) A blood pressure sensor comprising:
 a sensor including:
 a film portion, the film portion being deformable;
 a first sensing element fixed to the film portion, the first sensing element including a first magnetic layer of a first material, a first opposing magnetic layer, and a first intermediate layer, the first intermediate layer being provided between the first magnetic layer and the first opposing magnetic layer; and
 a second sensing element fixed to the film portion, the second sensing element including a second magnetic layer of a second material, a second opposing magnetic layer, and a second intermediate layer, the second material being different from the first material, the second intermediate layer being provided between the second magnetic layer and the second opposing magnetic layer.

(Configuration 25) A touch panel comprising:
 a sensor including:
 a film portion, the film portion being deformable;
 a first sensing element fixed to the film portion, the first sensing element including a first magnetic layer of a first material, a first opposing magnetic layer, and a first intermediate layer, the first intermediate layer being provided between the first magnetic layer and the first opposing magnetic layer; and
 a second sensing element fixed to the film portion, the second sensing element including a second magnetic layer of a second material, a second opposing magnetic layer, and a second intermediate layer, the second material being different from the first material, the second intermediate layer being provided between the second magnetic layer and the second opposing magnetic layer.

(Configuration 26) A electronic device comprising:
 a sensor including:
 a film portion, the film portion being deformable;
 a first sensing element fixed to the film portion, the first sensing element including a first magnetic layer of a first material, a first opposing magnetic layer, and a first intermediate layer, the first intermediate layer being provided between the first magnetic layer and the first opposing magnetic layer; and
 a second sensing element fixed to the film portion, the second sensing element including a second magnetic layer of a second material, a second opposing magnetic layer, and a second intermediate layer, the second material being different from the first material, the second intermediate layer being provided between the second magnetic layer and the second opposing magnetic layer.

According to the embodiments, a pressure sensor, an electronic device a microphone, a blood pressure sensor, and a touch panel in which the dynamic range can be enlarged can be provided.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in pressure sensors such as film portions, sensing elements, magnetic layers, intermediate layers, electrodes, processors, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all pressure sensors, electronic devices, microphones, blood pressure sensors, and touch panels practicable by an appropriate design modification by one skilled in the art based on the pressure sensors, the electronic devices, the microphones, the blood pressure sensors, and the touch panels described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a film portion, the film portion being deformable;
a first sensing element fixed to the film portion, the first sensing element including a first magnetic layer of a first material, a first opposing magnetic layer, and a first intermediate layer, the first intermediate layer being provided between the first magnetic layer and the first opposing magnetic layer; and
a second sensing element fixed to the film portion, the second sensing element including a second magnetic layer of a second material, a second opposing magnetic layer, and a second intermediate layer, the second material being different from the first material, the second intermediate layer being provided between the second magnetic layer and the second opposing magnetic layer.

2. The sensor according to claim 1, wherein a gauge factor of the first sensing element is different from a gauge factor of the second sensing element.

3. The sensor according to claim 1, wherein a sensitivity of the first sensing element is different from a sensitivity of the second sensing element.

4. The sensor according to claim 1, wherein
the first magnetic layer includes at least one of Fe, Co, or Ni with a first concentration, and
the second magnetic layer includes the at least one of Fe, Co, or Ni with a second concentration different from the first concentration.

5. The sensor according to claim 1, wherein
the first magnetic layer includes Fe,
the second magnetic layer includes Fe, and
a concentration of Fe in the second magnetic layer is different from a concentration of Fe in the first magnetic layer.

6. The sensor according to claim 1, wherein
the first magnetic layer includes at least one of Fe, Co, or Ni, and B,
the second magnetic layer includes at least one of Fe, Co, or Ni, and B, and
a concentration of B in the second magnetic layer is lower than a concentration of B in the first magnetic layer.

7. The sensor according to claim 5, wherein
the first magnetic layer includes an amorphous region, and
the second magnetic layer includes a crystal region.

8. The sensor according to claim 7, wherein
a concentration of the amorphous region in the first magnetic layer is higher than a concentration of the crystal region in the first magnetic layer.

9. The sensor according to claim 8, wherein
a concentration of the crystal region in the second magnetic layer is higher than a concentration of the amorphous region in the second magnetic layer.

10. The sensor according to claim 1, wherein
a composition ratio of Fe of the first magnetic layer is not less than 60 at. % and not more than 100 at. %, and
a composition ratio of Fe of the second magnetic layer is not less than 0 at. % but less than 60 at. %.

11. The sensor according to claim 1, wherein
a composition ratio of B of the first magnetic layer is not less than 10 at. % and not more than 30 at. %, and
a composition ratio of B of the second magnetic layer is not less than 0 at. % but less than 10 at. %.

12. The sensor according to claim 1, wherein
a first magnetization of the first magnetic layer changes according to a deformation of the film portion, and
a second magnetization of the second magnetic layer changes according to the deformation of the film portion.

13. The sensor according to claim 1, wherein a resistance between the first magnetic layer and the first opposing magnetic layer changes according to a deformation of the film portion.

14. The sensor according to claim 13, wherein a sensitivity of the resistance between the first magnetic layer and the first opposing magnetic layer with respect to the deformation is higher than a sensitivity of the resistance between the second magnetic layer and the second opposing magnetic layer with respect to the deformation.

15. The sensor according to claim 1, wherein
the first sensing element is most proximal to a first portion of an outer edge of the film portion,
the second sensing element is most proximal to a second portion of the outer edge, and
a difference between a first spacing and a second spacing is not more than 0.2 times the first spacing, the first spacing being between the first sensing element and the first portion, the second spacing being between the second sensing element and the second portion.

16. The sensor according to claim 1, further comprising a processor connected to the first sensing element and the second sensing element,
the processor implementing a first operation and a second operation, the first operation outputting a first output signal corresponding to a first signal obtained from the first sensing element, the second operation outputting a second output signal corresponding to a second signal obtained from the second sensing element.

17. The sensor according to claim 1, further comprising:
a substrate; and
a cover,
the film portion, first sensing element, and the second sensing element being provided between the substrate and the cover.

18. The sensor according to claim 1, wherein the second sensing element overlaps the first sensing element in a direction from the film portion toward the first sensing element.

19. A sensor, comprising:
a film portion, the film portion being deformable;
a first sensing element fixed to the film portion, the first sensing element including a first magnetic layer, a first opposing magnetic layer, and a first intermediate layer, the first intermediate layer being provided between the first magnetic layer and the first opposing magnetic layer;
a second sensing element fixed to the film portion, the second sensing element including a second magnetic layer, a second opposing magnetic layer, and a second intermediate layer, the second intermediate layer being provided between the second magnetic layer and the second opposing magnetic layer; and
a processor connected to the first sensing element and the second sensing element, the processor implementing a first operation and a second operation, the first operation outputting a first output signal corresponding to a first signal obtained from the first sensing element, the second operation outputting a second output signal corresponding to a second signal obtained from the second sensing element.

20. The sensor according to claim 19, wherein the processor implements the first operation when a first amplitude of the first signal is wider than a second amplitude of the second signal and implements the second operation when the second amplitude is wider than the first amplitude.

\* \* \* \* \*